(12) United States Patent
Lion et al.

(10) Patent No.: US 10,792,241 B2
(45) Date of Patent: *Oct. 6, 2020

(54) COSMETIC PROCESS FOR TREATING KERATIN MATERIALS WITH A MALEIC ANHYDRIDE ETHYLENIC POLYMER

(71) Applicant: L'OREAL, Paris (FR)

(72) Inventors: Bertrand Lion, Aulnay-sous-Bois (FR); Julien Portal, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 28 days.

This patent is subject to a terminal disclaimer.

(21) Appl. No.: 16/063,602

(22) PCT Filed: Dec. 16, 2016

(86) PCT No.: PCT/EP2016/081356
§ 371 (c)(1),
(2) Date: Jun. 18, 2018

(87) PCT Pub. No.: WO2017/108602
PCT Pub. Date: Jun. 29, 2017

(65) Prior Publication Data
US 2018/0369123 A1    Dec. 27, 2018

(30) Foreign Application Priority Data

Dec. 22, 2015 (FR) ...................... 15 63118

(51) Int. Cl.
| | |
|---|---|
| *A61K 8/81* | (2006.01) |
| *A61K 8/41* | (2006.01) |
| *A61Q 1/06* | (2006.01) |
| *A61K 8/58* | (2006.01) |
| *A61K 8/898* | (2006.01) |
| *A61K 8/31* | (2006.01) |
| *A61Q 1/02* | (2006.01) |
| *A61Q 1/10* | (2006.01) |
| *A61K 8/37* | (2006.01) |
| *C08F 220/18* | (2006.01) |
| *C08F 222/06* | (2006.01) |
| *C08F 290/06* | (2006.01) |

(52) U.S. Cl.
CPC .............. *A61K 8/8152* (2013.01); *A61K 8/31* (2013.01); *A61K 8/37* (2013.01); *A61K 8/41* (2013.01); *A61K 8/585* (2013.01); *A61K 8/8141* (2013.01); *A61K 8/898* (2013.01); *A61Q 1/02* (2013.01); *A61Q 1/06* (2013.01); *A61Q 1/10* (2013.01); *A61K 2800/882* (2013.01); *A61K 2800/884* (2013.01); *A61K 2800/95* (2013.01); *C08F 220/18* (2013.01); *C08F 222/06* (2013.01); *C08F 290/068* (2013.01)

(58) Field of Classification Search
None
See application file for complete search history.

(56) References Cited

U.S. PATENT DOCUMENTS

| | | | |
|---|---|---|---|
| 4,503,182 A | 3/1985 | Durand et al. | |
| 4,731,095 A | 3/1988 | Garapon et al. | |
| 5,064,922 A | 11/1991 | Wamprecht et al. | |
| 5,130,378 A | 7/1992 | Blum et al. | |
| 2001/0025094 A1 | 9/2001 | Gunther et al. | |
| 2003/0124074 A1* | 7/2003 | Mougin ................. | A61K 8/046 424/61 |
| 2009/0047308 A1* | 2/2009 | Farcet .................. | A61K 8/8152 424/401 |
| 2010/0120931 A1 | 5/2010 | Zajaczkowski et al. | |
| 2012/0171140 A1* | 7/2012 | Bui ........................ | A61K 8/898 424/64 |
| 2013/0213426 A1 | 8/2013 | Bui et al. | |
| 2013/0224134 A1 | 8/2013 | Bui et al. | |
| 2015/0044790 A1 | 2/2015 | Tsai | |

FOREIGN PATENT DOCUMENTS

| | | |
|---|---|---|
| FR | 2 582 057 A1 | 12/1986 |
| WO | WO-2012/089798 A1 | 7/2012 |

* cited by examiner

*Primary Examiner* — Jessica Worsham
(74) *Attorney, Agent, or Firm* — Polsinelli PC

(57) ABSTRACT

The invention relates to a cosmetic process for treating keratin materials, comprising: either the sequential application to the keratin materials of a composition comprising a maleic anhydride ethylenic polymer and of an amine compound chosen from polyamine compounds bearing several primary amine and/or secondary amine groups and amino alkoxysilanes, or the topical application to the keratin materials of a composition derived from the mixing of a composition comprising a maleic anhydride acrylic polymer and of an amine compound chosen from amino alkoxysilanes; the ethylenic polymer being derived from the polymerization of: (a) 45% to 95% by weight, relative to the total weight of monomers, of an ethylenic monomer bearing an at least C8 linear or branched alkyl group; (b) 5% to 25% by weight of maleic anhydride; (c) 0 to 50% by weight of additional monomer; the compositions used being anhydrous when the amine compound is an amino alkoxysilane. The process makes it possible to obtain a film-forming deposit that has good resistance to water, to oil and to sebum. The film is also non-tacky and transfer-resistant.

38 Claims, No Drawings

COSMETIC PROCESS FOR TREATING KERATIN MATERIALS WITH A MALEIC ANHYDRIDE ETHYLENIC POLYMER

CROSS REFERENCE TO RELATED APPLICATIONS

This application is the National Phase of Application No. PCT/EP2016/081356 filed Dec. 16, 2016, which claims priority to Application No. 15 63118 filed in France on Dec. 22, 2015 under 35 U.S.C. § 119. The entire contents of each application are hereby incorporated by reference.

The present invention relates to a cosmetic process for treating keratin materials using a maleic anhydride acrylic polymer, and also to a kit for performing said process, and to certain novel polymers.

Cosmetic products often require the use of a film-forming polymer to obtain a deposit of the product on keratin materials that has good cosmetic properties. In particular, it is necessary for the film-forming deposit to have good persistence, in particular for the deposit not to transfer during contact with the fingers, clothing, a glass or a cup, and also good persistence on contact with water, especially rain or during showering or alternatively perspiration. Skin sebum may also damage the film-forming deposit.

It is known to those skilled in the art to use polymers in order to obtain these good persistence properties throughout the day. These polymers are of very different chemical nature and are generally conveyed either in a fatty phase or in an aqueous phase. Examples that may be mentioned include silicone resins, polyacrylates and lattices.

Although these polymers do indeed afford persistence properties, in particular transfer resistance, they may have a certain level of discomfort: for example, after applying the product, they may have a tacky aspect.

There is thus still a need for polymers that can afford good persistence properties while at the same time maintaining a certain level of comfort during use.

The inventors have discovered that a process for treating keratin materials using a particular maleic anhydride ethylenic polymer combined with a particular amine compound makes it possible to obtain a deposit on keratin materials that has good film-forming properties.

The film-forming deposit obtained has good water resistance and also good resistance to oil (especially to olive oil) and to sebum.

In addition, the film obtained has good flexibility to follow the deformations of the skin without becoming impaired.

The particular ethylenic polymer is readily conveyable in a hydrocarbon-based oil such as isododecane.

Furthermore, the film-forming deposit has good tack-resistance and transfer-resistance properties, especially when the film is touched with the fingers: the deposit obtained thus has good persistence properties.

Furthermore, when the maleic anhydride ethylenic polymer is formulated with a non-volatile oil (often used in makeup products), for instance 2-octylethanol, the process according to the invention makes it possible to obtain a film-forming deposit which has good persistence, transfer-resistance, tack-resistance, water-resistance, oil-resistance and sebum-resistance properties.

The maleic anhydride ethylenic polymer combined with said polyamine compound forms a film-forming deposit that is suitable for making up the skin or the lips, such as foundations or lipsticks.

U.S. Pat. No. 4,731,095 describes copolymers of C22-C28 alpha-olefin, maleic anhydride and 2-ethylhexyl acrylate which react with 1,3-diaminopropane-based polyamines. U.S. Pat. No. 4,503,182 describes copolymers of C18-C22 alkyl acrylate, maleic anhydride and diisobutylene which react with N-alkylpropylenediamine or N-3-octyloxypropyl-1,3-diaminopropane. The products obtained are used as additive for hydrocarbon distillates such as fuel.

U.S. Pat. No. 5,064,922 describes copolymers of 2-ethylhexyl methacrylate, maleic anhydride and styrene which react with 1-amino-1-methyl-4-aminomethylcyclohexane. The product obtained is used as a binder in paints or inks.

FR 2 583 057 describes copolymers of maleic anhydride, diisobutylene and C16-C22 alkyl (meth)acrylate which react with dimethylaminopropylamine. The product obtained is used as a fuel additive.

More precisely, a subject of the present invention is a process, especially a cosmetic process, for treating, especially for caring for or making up, the keratin materials, in particular human keratin materials, comprising:

either the sequential application to the keratin materials of a composition comprising a maleic anhydride ethylenic polymer and of an amine compound chosen from polyamine compounds bearing several primary amine and/or secondary amine groups and amino alkoxysilanes, or of a composition containing it and comprising a physiologically acceptable medium, or the topical application to the keratin materials of a composition derived from the mixing of a composition comprising a maleic anhydride ethylenic polymer and of an amine compound chosen from amino alkoxysilanes, or of a composition containing it and comprising a physiologically acceptable medium;

the ethylenic polymer being derived from the polymerization of, or consisting of:

(a) 45% to 95% by weight, relative to the total weight of monomers, of an ethylenic monomer bearing an at least $C_8$ linear or branched alkyl group;

(b) 5% to 25% by weight of maleic anhydride;

(c) 0 to 50% by weight of additional monomer chosen from:

(i) polydimethylsiloxane silicone monomers bearing a mono(meth)acryloyloxy end group as defined below;

(ii) linear or branched $C_1$-$C_6$ alkyl (meth)acrylate or $C_6$-$C_{12}$ cycloalkyl (meth)acrylate non-silicone monomers;

the compositions used being anhydrous when the amine compound is an amino alkoxysilane.

According to one embodiment of the process according to the invention, the ethylenic polymer used consists of the monomers described previously, in the described contents.

According to a first embodiment of the process according to the invention, a composition comprising an ethylenic polymer and an amine compound as defined previously, or a composition containing it and comprising a physiologically acceptable medium, as defined previously, are applied sequentially to the keratin materials, the compositions used being anhydrous when the amine compound is an amino alkoxysilane.

According to one embodiment of the process according to the invention, the composition comprising the ethylenic polymer is applied first to the keratin materials, and said amine compound or a composition containing it and comprising a physiologically acceptable medium is then applied.

According to another embodiment, said amine compound, or a composition containing it and comprising a physiologically acceptable medium, is applied first to the keratin materials, and the composition comprising the ethylenic polymer is then applied.

According to a second embodiment of the process according to the invention, a composition derived from the mixing (extemporaneous) of a composition comprising an ethylenic polymer and of an amine compound, or of a composition containing it and comprising a physiologically acceptable medium, as are defined previously, is applied topically to the keratin materials, the composition derived from the mixing being anhydrous when the amine compound is an amino alkoxysilane.

According to one embodiment of the process according to the invention, the mixing of the composition comprising the ethylenic polymer and of the amine compound, or of the composition containing it, is performed in a time of between 1 minute and 24 hours before its application to the keratin materials, and preferably between 5 and 30 minutes.

A subject of the invention is also a composition, especially a cosmetic composition, obtained by mixing an ethylenic polymer or a composition containing it and comprising a physiologically acceptable medium, and an amine compound or a composition containing it and comprising a physiologically acceptable medium, as are described previously, the composition being anhydrous when the amine compound is an amino alkoxysilane.

A subject of the invention is also a kit comprising a first composition comprising said maleic anhydride ethylenic polymer as described previously and a second composition comprising an amine compound as described previously and optionally comprising a physiologically acceptable medium, the first and second compositions each being packaged in a separate packaging assembly, the compositions being anhydrous when the amine compound is an amino alkoxysilane.

The composition packaging assembly is, in a known manner, any packaging that is suitable for storing cosmetic compositions (in particular a bottle, tube, spray bottle or aerosol bottle).

Such a kit allows the process for treating keratin materials according to the invention to be performed.

The ethylenic polymer used according to the invention comprises an ethylenic monomer bearing an at least $C_8$ linear or branched alkyl group (referred to as a fatty-chain ethylenic monomer); said alkyl group may be a linear or branched $C_8$-$C_{22}$ or $C_8$ to $C_{12}$ alkyl group.

Such a fatty-chain ethylenic monomer may be chosen from:
a) linear or branched $C_8$-$C_{22}$ alkyl (meth)acrylates (i.e. comprising a $C_8$-$C_{22}$ alkyl group);
b) the (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group;
c) the vinyl esters of formula $R_5$—O—CH—CH=$CH_2$ in which $R_5$ represents a linear or branched $C_8$-$C_{22}$ alkyl group;
d) the ethers of formula $R_6$—O—CH=$CH_2$ in which $R_6$ represents a linear or branched $C_8$-$C_{22}$ alkyl group.

Linear or branched $C_8$-$C_{22}$ alkyl groups that may be mentioned include octyl, 2-ethylhexyl, isooctyl, nonyl, decyl, undecyl, lauryl, myristyl, palmityl, stearyl, eicosyl and behenyl radicals, and especially a 2-ethylhexyl, lauryl, behenyl or stearyl group.

Preferably, the fatty-chain ethylenic monomer is chosen from $C_8$-$C_{22}$ and especially $C_8$-$C_{18}$ alkyl (meth)acrylates, for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

2-Ethylhexyl acrylate, 2-ethylhexyl methacrylate, stearyl acrylate or stearyl methacrylate is preferably used.

2-Ethylhexyl acrylate is preferentially used.

The fatty-chain monomer may be present in said ethylenic polymer in a content ranging from 45% to 90% by weight and preferably ranging from 50% to 90% by weight, relative to the total weight of monomers.

In the absence of additional monomer in the ethylenic polymer, the fatty-chain monomer may be present in a content ranging from 75% to 95% by weight, preferably ranging from 75% to 90% by weight and preferentially ranging from 78% to 87% by weight, relative to the total weight of monomers.

In the presence of additional monomer in the ethylenic polymer, the fatty-chain monomer may be present in a content ranging from 45% to 94.5% by weight, preferably ranging from 45% to 90% by weight, preferentially ranging from 50% to 75% by weight and more preferentially ranging from 52% to 67% by weight, relative to the total weight of monomers.

The ethylenic polymer used according to the invention contains maleic anhydride.

Maleic anhydride may be present in said ethylenic polymer in a content ranging from 10% to 25% by weight and preferably ranging from 13% to 22% by weight, relative to the total weight of monomers.

The additional silicone monomer is a polydimethylsiloxane bearing a mono(meth)acryloyloxy end group of formula (I) (referred to hereinbelow as a silicone monomer) below:

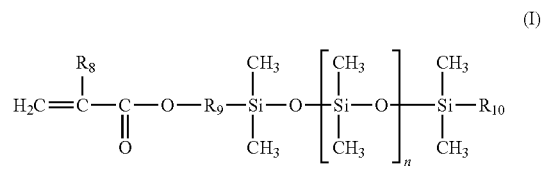

in which:
$R_8$ denotes a hydrogen atom or a methyl group; preferably methyl;
$R_9$ denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;
$R_{10}$ denotes a linear or branched alkyl group containing from 1 to 10 carbon atoms, especially from 2 to 8 carbon atoms; preferably methyl, ethyl, propyl, butyl or pentyl;
n denotes an integer ranging from 1 to 300, preferably ranging from 3 to 200 and preferentially ranging from 5 to 100.

Use may be made in particular of monomethacryloyloxypropyl polydimethylsiloxanes such as those sold under the names MCR-M07, MCR-M17, MCR-M11 and MCR-M22 by Gelest Inc or the silicone macromonomers sold under the names X-22-2475, X-22-2426 and X-22-174DX by Shin-Etsu.

The additional silicone monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight.

The additional non-silicone monomer chosen from linear or branched $C_1$-$C_6$ alkyl (meth)acrylates may be, for example, methyl (meth)acrylate, ethyl (meth)acrylate, propyl (meth)acrylate, n-butyl (meth)acrylate, isobutyl (meth)acrylate, pentyl (meth)acrylate or hexyl (meth)acrylate. Methyl (meth)acrylate or ethyl (meth)acrylate is preferably used.

The $C_6$-$C_{12}$ cycloalkyl (meth)acrylate is preferably isobornyl (meth)acrylate.

The additional non-silicone monomer may be present in said ethylenic polymer in a content ranging from 0.5% to 50% by weight, relative to the total weight of monomers, preferably ranging from 5% to 50% by weight, preferentially ranging from 15% to 40% by weight and more preferentially ranging from 20% to 35% by weight.

According to one embodiment of the invention, the ethylenic polymer does not comprise any additional monomer: it is formed from ethylenic monomer bearing an at least $C_8$ linear or branched alkyl group and maleic anhydride.

According to another embodiment of the invention, the ethylenic polymer comprises at least one additional monomer as defined previously. The additional monomer may be present in said ethylenic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to another embodiment of the invention, the ethylenic polymer comprises at least one additional silicone monomer as defined previously.

According to another embodiment of the invention, the ethylenic polymer comprises at least one additional non-silicone monomer as defined previously. Preferably, it is a $C_6$-$C_{12}$ cycloalkyl (meth)acrylate.

According to another embodiment of the invention, the ethylenic polymer comprises at least one additional silicone monomer and at least one additional non-silicone monomer as defined previously.

According to a first embodiment of the invention, the ethylenic polymer comprises, or consists of:
(a) 75% to 95% by weight, relative to the total weight of monomers, of linear or branched $C_8$-$C_{22}$ alkyl (meth)acrylate;
(b) 5% to 25% by weight of maleic anhydride.

The ethylenic polymer especially comprises, or consists of:
(a) 75% to 95% by weight, relative to the total weight of monomers, of linear or branched $C_8$-$C_{18}$ alkyl (meth)acrylate;
(b) 5% to 25% by weight of maleic anhydride.

In particular, the ethylenic polymer comprises, or consists of:
(a) 75% to 95% by weight, relative to the total weight of monomers, of 2-ethylhexyl (meth)acrylate;
(b) 5% to 25% by weight of maleic anhydride.

In particular, the ethylenic polymer comprises, or consists of:
(a) 75% to 95% by weight, relative to the total weight of monomers, of stearyl (meth)acrylate;
(b) 5% to 25% by weight of maleic anhydride.

In particular, the ethylenic polymer comprises, or consists of:
(a) 75% to 95% by weight, relative to the total weight of monomers, of a mixture of 2-ethylhexyl (meth)acrylate and of stearyl (meth)acrylate;
(b) 5% to 25% by weight of maleic anhydride.

Preferably, the ethylenic polymer comprises, or consists of:
(a) 75% to 90% by weight, relative to the total weight of monomers, of linear or branched $C_8$-$C_{22}$ alkyl (meth)acrylate;
(b) 10% to 25% by weight of maleic anhydride.

The ethylenic polymer especially comprises, or consists of:
(a) 75% to 90% by weight, relative to the total weight of monomers, of linear or branched $C_8$-$C_{18}$ alkyl (meth)acrylate;
(b) 10% to 25% by weight of maleic anhydride.

In particular, the ethylenic polymer comprises, or consists of:
(a) 75% to 90% by weight, relative to the total weight of monomers, of 2-ethylhexyl (meth)acrylate;
(b) 10% to 25% by weight of maleic anhydride.

In particular, the ethylenic polymer comprises, or consists of:
(a) 75% to 90% by weight, relative to the total weight of monomers, of stearyl (meth)acrylate;
(b) 10% to 25% by weight of maleic anhydride.

In particular, the ethylenic polymer comprises, or consists of:
(a) 75% to 90% by weight, relative to the total weight of monomers, of a mixture of 2-ethylhexyl (meth)acrylate and of stearyl (meth)acrylate;
(b) 10% to 25% by weight of maleic anhydride.

Preferentially, the ethylenic polymer comprises, or consists of:
(a) 78% to 87% by weight, relative to the total weight of monomers, of linear or branched $C_8$-$C_{22}$ alkyl (meth)acrylate;
(b) 13% to 22% by weight of maleic anhydride.

The ethylenic polymer especially comprises, or consists of:
(a) 78% to 87% by weight, relative to the total weight of monomers, of linear or branched $C_8$-$C_{18}$ alkyl (meth)acrylate;
(b) 13% to 22% by weight of maleic anhydride.

In particular, the ethylenic polymer comprises, or consists of:
(a) 78% to 87% by weight, relative to the total weight of monomers, of 2-ethylhexyl (meth)acrylate;
(b) 13% to 22% by weight of maleic anhydride.

In particular, the ethylenic polymer comprises, or consists of:
(a) 78% to 87% by weight, relative to the total weight of monomers, of stearyl (meth)acrylate;
(b) 13% to 22% by weight of maleic anhydride.

In particular, the ethylenic polymer comprises, or consists of:
(a) 78% to 87% by weight, relative to the total weight of monomers, of a mixture of 2-ethylhexyl (meth)acrylate and of stearyl (meth)acrylate;
(b) 13% to 22% by weight of maleic anhydride.

The ethylenic polymer may be chosen from the following copolymers:
2-ethylhexyl acrylate/maleic anhydride (85/15 by weight)
2-ethylhexyl acrylate/maleic anhydride (80/20 by weight)

2-ethylhexyl acrylate/stearyl acrylate/maleic anhydride (50/30/20 by weight)

According to a second embodiment of the invention, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of silicone monomer (I) as described previously.

The ethylenic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of silicone monomer (I) as described previously.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of silicone monomer (I) as described previously.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of silicone monomer (I) as described previously.

The ethylenic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of silicone monomer (I) as described previously.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of silicone monomer (I) as described previously.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of silicone monomer (I) as described previously.

The ethylenic polymer especially comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of silicone monomer (I) as described previously.

In particular, the ethylenic polymer comprises, or consists of:
(a) 50% to 75% by weight, relative to the total weight of monomers, of a mixture of 2-ethylhexyl (meth)acrylate and of stearyl (meth)acrylate;
(b) 10% to 25% by weight of maleic anhydride;
(c) 15% to 40% by weight of silicone monomer (I) as described previously.

More preferentially, the ethylenic polymer comprises, or consists of:
(a) 52% to 67% by weight, relative to the total weight of monomers, of linear or branched $C_8$-$C_{22}$ alkyl (meth)acrylate;
(b) 13% to 22% by weight of maleic anhydride;
(c) 20% to 35% by weight of silicone monomer (I) as described previously.

The ethylenic polymer especially comprises, or consists of:
(a) 52% to 67% by weight, relative to the total weight of monomers, of linear or branched $C_8$-$C_{18}$ alkyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of 2-ethylhexyl (meth)acrylate;
(b) 13% to 22% by weight of maleic anhydride;

(c) 20% to 35% by weight of silicone monomer (I) as described previously.

In particular, the ethylenic polymer comprises, or consists of:
(a) 52% to 67% by weight, relative to the total weight of monomers, of stearyl (meth)acrylate;
(b) 13% to 22% by weight of maleic anhydride;
(c) 20% to 35% by weight of silicone monomer (I) as described previously.

In particular, the ethylenic polymer comprises, or consists of:
(a) 52% to 67% by weight, relative to the total weight of monomers, of a mixture of 2-ethylhexyl (meth)acrylate and of stearyl (meth)acrylate;
(b) 13% to 22% by weight of maleic anhydride;
(c) 20% to 35% by weight of silicone monomer (I) as described previously.

The ethylenic polymer may be chosen from the following copolymers:
2-ethylhexyl acrylate/maleic anhydride/silicone monomer (I)
stearyl acrylate/maleic anhydride/silicone monomer (I)
2-ethylhexyl acrylate/stearyl acrylate/maleic anhydride/silicone monomer (I)
in the respective monomer contents described previously, and in particular:
the 2-ethylhexyl acrylate/PDMS methacrylate/maleic anhydride copolymer (50/30/20 by weight).

According to a third embodiment of the invention, the ethylenic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of maleic anhydride;
(c) 0.5% to 50% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride;
(c) 0.5% to 50% by weight of $C_6$-$C_{12}$ cycloalkyl (meth)acrylate.

In particular, the ethylenic polymer comprises, or consists of:
(a) 45% to 94.5% by weight, relative to the total weight of monomers, of 2-ethylhexyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of stearyl (meth)acrylate;
(b) 5% to 25% by weight of maleic anhydride;
(c) 0.5% to 50% by weight of isobornyl (meth)acrylate.

In particular, the ethylenic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of maleic anhydride;
(c) 0.5% to 50% by weight of isobornyl (meth)acrylate.

Preferably, the ethylenic polymer comprises, or consists of:
(a) 45% to 90% by weight, relative to the total weight of monomers, of linear or branched $C_8$-$C_{22}$ alkyl (meth)acrylate;
(b) 5% to 25% by weight of maleic anhydride;
(c) 5% to 50% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of maleic anhydride;
(c) 5% to 50% by weight of $C_6$-$C_{12}$ cycloalkyl (meth)acrylate.

In particular, the ethylenic polymer comprises, or consists of:
(a) 45% to 90% by weight, relative to the total weight of monomers, of 2-ethylhexyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of stearyl (meth)acrylate;
(b) 5% to 25% by weight of maleic anhydride;
(c) 5% to 50% by weight of isobornyl (meth)acrylate.

In particular, the ethylenic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of maleic anhydride;
(c) 5% to 50% by weight of isobornyl (meth)acrylate.

Preferentially, the ethylenic polymer comprises, or consists of:
(a) 50% to 75% by weight, relative to the total weight of monomers, of linear or branched $C_8$-$C_{22}$ alkyl (meth)acrylate;
(b) 10% to 25% by weight of maleic anhydride;
(c) 15% to 40% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:
(a) 50% to 75% by weight, relative to the total weight of monomers, of linear or branched $C_8$-$C_{18}$ alkyl (meth)acrylate;
(b) 10% to 25% by weight of maleic anhydride;
(c) 15% to 40% by weight of $C_6$-$C_{12}$ cycloalkyl (meth)acrylate.

In particular, the ethylenic polymer comprises, or consists of:
(a) 50% to 75% by weight, relative to the total weight of monomers, of 2-ethylhexyl (meth)acrylate;
(b) 10% to 25% by weight of maleic anhydride;
(c) 15% to 40% by weight of isobornyl (meth)acrylate.

In particular, the ethylenic polymer comprises, or consists of:
(a) 50% to 75% by weight, relative to the total weight of monomers, of stearyl (meth)acrylate;
(b) 10% to 25% by weight of maleic anhydride;
(c) 15% to 40% by weight of isobornyl (meth)acrylate.

In particular, the ethylenic polymer comprises, or consists of:

(a) 50% to 75% by weight, relative to the total weight of monomers, of a mixture of 2-ethylhexyl (meth)acrylate and of stearyl (meth)acrylate;

(b) 10% to 25% by weight of maleic anhydride;

(c) 15% to 40% by weight of isobornyl (meth)acrylate.

More preferentially, the ethylenic polymer comprises, or consists of:

(a) 52% to 67% by weight, relative to the total weight of monomers, of linear or branched $C_8$-$C_{22}$ alkyl (meth)acrylate;

(b) 13% to 22% by weight of maleic anhydride;

(c) 20% to 35% by weight of additional non-silicone monomer chosen from linear or branched $C_1$-$C_6$ alkyl (meth)acrylates or $C_6$-$C_{12}$ cycloalkyl (meth)acrylates.

The ethylenic polymer especially comprises, or consists of:

(a) 52% to 67% by weight, relative to the total weight of monomers, of linear or branched $C_8$-$C_{18}$ alkyl (meth)acrylate;

(b) 13% to 22% by weight of maleic anhydride;

(c) 20% to 35% by weight of $C_6$-$C_{12}$ cycloalkyl (meth)acrylate.

In particular, the ethylenic polymer comprises, or consists of:

(a) 52% to 67% by weight, relative to the total weight of monomers, of 2-ethylhexyl (meth)acrylate;

(b) 13% to 22% by weight of maleic anhydride;

(c) 20% to 35% by weight of isobornyl (meth)acrylate.

In particular, the ethylenic polymer comprises, or consists of:

(a) 52% to 67% by weight, relative to the total weight of monomers, of stearyl (meth)acrylate;

(b) 13% to 22% by weight of maleic anhydride;

(c) 20% to 35% by weight of isobornyl (meth)acrylate.

In particular, the ethylenic polymer comprises, or consists of:

(a) 52% to 67% by weight, relative to the total weight of monomers, of a mixture of 2-ethylhexyl (meth)acrylate and of stearyl (meth)acrylate;

(b) 13% to 22% by weight of maleic anhydride;

(c) 20% to 35% by weight of isobornyl (meth)acrylate.

The ethylenic polymer may be chosen from the following copolymers:

2-ethylhexyl acrylate/maleic anhydride/isobornyl (meth)acrylate stearyl acrylate/maleic anhydride/isobornyl (meth)acrylate 2-ethylhexyl acrylate/stearyl acrylate/maleic anhydride/isobornyl (meth)acrylate in the respective monomer contents described previously.

According to a fourth embodiment of the invention, the ethylenic polymer comprises, or consists of:

(a) 45% to 94.5% by weight, relative to the total weight of monomers, of linear or branched $C_8$-$C_{22}$ alkyl (meth)acrylate;

(b) 5% to 25% by weight of maleic anhydride;

(c) 0.5% to 50% by weight of a mixture of additional non-silicone monomer chosen from $C_6$-$C_{12}$ cycloalkyl (meth)acrylates and of silicone monomer (I) as described previously.

The ethylenic polymer especially comprises, or consists of:

(a) 45% to 94.5% by weight, relative to the total weight of monomers, of linear or branched $C_8$-$C_{18}$ alkyl (meth)acrylate;

(b) 5% to 25% by weight of maleic anhydride;

(c) 0.5% to 50% by weight of a mixture of $C_6$-$C_{12}$ cycloalkyl (meth)acrylate and of silicone monomer (I) as described previously.

In particular, the ethylenic polymer comprises, or consists of:

(a) 45% to 94.5% by weight, relative to the total weight of monomers, of 2-ethylhexyl (meth)acrylate;

(b) 5% to 25% by weight of maleic anhydride;

(c) 0.5% to 50% by weight of a mixture of isobornyl (meth)acrylate and of silicone monomer (I) as described previously.

In particular, the ethylenic polymer comprises, or consists of:

(a) 45% to 94.5% by weight, relative to the total weight of monomers, of stearyl (meth)acrylate;

(b) 5% to 25% by weight of maleic anhydride;

(c) 0.5% to 50% by weight of a mixture of isobornyl (meth)acrylate and of silicone monomer (I) as described previously.

In particular, the ethylenic polymer comprises, or consists of:

(a) 45% to 94.5% by weight, relative to the total weight of monomers, of a mixture of 2-ethylhexyl (meth)acrylate and of stearyl (meth)acrylate;

(b) 5% to 25% by weight of maleic anhydride;

(c) 0.5% to 50% by weight of a mixture of isobornyl (meth)acrylate and of silicone monomer (I) as described previously.

Preferably, the ethylenic polymer comprises, or consists of:

(a) 45% to 90% by weight, relative to the total weight of monomers, of linear or branched $C_8$-$C_{22}$ alkyl (meth)acrylate;

(b) 5% to 25% by weight of maleic anhydride;

(c) 5% to 50% by weight of a mixture of additional non-silicone monomer chosen from linear or branched $C_1$-$C_6$ alkyl (meth)acrylates or $C_6$-$C_{12}$ cycloalkyl (meth)acrylates and of silicone monomer (I) as described previously.

The ethylenic polymer especially comprises, or consists of:

(a) 45% to 90% by weight, relative to the total weight of monomers, of linear or branched $C_8$-$C_{18}$ alkyl (meth)acrylate;

(b) 5% to 25% by weight of maleic anhydride;

(c) 5% to 50% by weight of a mixture of $C_6$-$C_{12}$ cycloalkyl (meth)acrylate and of silicone monomer (I) as described previously.

In particular, the ethylenic polymer comprises, or consists of:

(a) 45% to 90% by weight, relative to the total weight of monomers, of 2-ethylhexyl (meth)acrylate;

(b) 5% to 25% by weight of maleic anhydride;

(c) 5% to 50% by weight of a mixture of isobornyl (meth)acrylate and of silicone monomer (I) as described previously.

In particular, the ethylenic polymer comprises, or consists of:

(a) 45% to 90% by weight, relative to the total weight of monomers, of stearyl (meth)acrylate;

(b) 5% to 25% by weight of maleic anhydride;

(c) 5% to 50% by weight of a mixture of isobornyl (meth)acrylate and of silicone monomer (I) as described previously.

In particular, the ethylenic polymer comprises, or consists of:
 (a) 45% to 90% by weight, relative to the total weight of monomers, of a mixture of 2-ethylhexyl (meth)acrylate and of stearyl (meth)acrylate;
 (b) 5% to 25% by weight of maleic anhydride;
 (c) 5% to 50% by weight of a mixture of isobornyl (meth)acrylate and of silicone monomer (I) as described previously.

Preferentially, the ethylenic polymer comprises, or consists of:
 (a) 50% to 75% by weight, relative to the total weight of monomers, of linear or branched $C_8$-$C_{22}$ alkyl (meth)acrylate;
 (b) 10% to 25% by weight of maleic anhydride;
 (c) 15% to 40% by weight of a mixture of additional non-silicone monomer chosen from linear or branched $C_1$-$C_6$ alkyl (meth)acrylates or $C_6$-$C_{12}$ cycloalkyl (meth)acrylates and of silicone monomer (I) as described previously.

The ethylenic polymer especially comprises, or consists of:
 (a) 50% to 75% by weight, relative to the total weight of monomers, of linear or branched $C_8$-$C_{18}$ alkyl (meth)acrylate;
 (b) 10% to 25% by weight of maleic anhydride;
 (c) 15% to 40% by weight of a mixture of $C_6$-$C_{12}$ cycloalkyl (meth)acrylate and of silicone monomer (I) as described previously.

In particular, the ethylenic polymer comprises, or consists of:
 (a) 50% to 75% by weight, relative to the total weight of monomers, of 2-ethylhexyl (meth)acrylate;
 (b) 10% to 25% by weight of maleic anhydride;
 (c) 15% to 40% by weight of a mixture of isobornyl (meth)acrylate and of silicone monomer (I) as described previously.

In particular, the ethylenic polymer comprises, or consists of:
 (a) 50% to 75% by weight, relative to the total weight of monomers, of stearyl (meth)acrylate;
 (b) 10% to 25% by weight of maleic anhydride;
 (c) 15% to 40% by weight of a mixture of isobornyl (meth)acrylate and of silicone monomer (I) as described previously.

In particular, the ethylenic polymer comprises, or consists of:
 (a) 50% to 75% by weight, relative to the total weight of monomers, of a mixture of 2-ethylhexyl (meth)acrylate and of stearyl (meth)acrylate;
 (b) 10% to 25% by weight of maleic anhydride;
 (c) 15% to 40% by weight of a mixture of isobornyl (meth)acrylate and of silicone monomer (I) as described previously.

More preferentially, the ethylenic polymer comprises, or consists of:
 (a) 52% to 67% by weight, relative to the total weight of monomers, of linear or branched $C_8$-$C_{22}$ alkyl (meth)acrylate;
 (b) 13% to 22% by weight of maleic anhydride;
 (c) 20% to 35% by weight of a mixture of additional non-silicone monomer chosen from linear or branched $C_1$-$C_6$ alkyl (meth) acrylates or $C_6$-$C_{12}$ cycloalkyl (meth) acrylates and of silicone monomer (I) as described previously.

The ethylenic polymer especially comprises, or consists of:
 (a) 52% to 67% by weight, relative to the total weight of monomers, of linear or branched $C_8$-$C_{18}$ alkyl (meth)acrylate;
 (b) 13% to 22% by weight of maleic anhydride;
 (c) 20% to 35% by weight of a mixture of $C_6$-$C_{12}$ cycloalkyl (meth)acrylate and of silicone monomer (I) as described previously.

In particular, the ethylenic polymer comprises, or consists of:
 (a) 52% to 67% by weight, relative to the total weight of monomers, of 2-ethylhexyl (meth)acrylate;
 (b) 13% to 22% by weight of maleic anhydride;
 (c) 20% to 35% by weight of a mixture of isobornyl (meth)acrylate and of silicone monomer (I) as described previously.

In particular, the ethylenic polymer comprises, or consists of:
 (a) 52% to 67% by weight, relative to the total weight of monomers, of stearyl (meth)acrylate;
 (b) 13% to 22% by weight of maleic anhydride;
 (c) 20% to 35% by weight of a mixture of isobornyl (meth)acrylate and of silicone monomer (I) as described previously.

In particular, the ethylenic polymer comprises, or consists of:
 (a) 52% to 67% by weight, relative to the total weight of monomers, of a mixture of 2-ethylhexyl (meth)acrylate and of stearyl (meth)acrylate;
 (b) 13% to 22% by weight of maleic anhydride;
 (c) 20% to 35% by weight of a mixture of isobornyl (meth)acrylate and of silicone monomer (I) as described previously.

The ethylenic polymer may be chosen from the following copolymers:
 2-ethylhexyl acrylate/maleic anhydride/isobornyl (meth)acrylate/silicone monomer (I)
 stearyl acrylate/maleic anhydride/isobornyl (meth)acrylate/silicone monomer (I)
 2-ethylhexyl acrylate/stearyl acrylate/maleic anhydride/isobornyl (meth)acrylate/silicone monomer (I)
in the respective monomer contents described previously.

Advantageously, the polymer used according to the invention consists of the monomers described previously.

Advantageously, the polymer used according to the invention is nonionic.

Preferably, the ethylenic polymer used according to the invention has a weight-average molecular weight ranging from 5000 to 1 000 000 g/mol, preferably ranging from 8000 to 500 000 g/mol and preferentially ranging from 10 000 to 350 000 g/mol.

The molecular weight may especially be determined by steric exclusion chromatography, with THF eluent, polystyrene standard, 2414 refractometric detector from Waters.

The copolymer may be a random, alternating (block) or gradient polymer. Preferably, the copolymer is random.

The copolymer used according to the invention may be prepared by radical polymerization of the monomers described previously, especially as a mixture or added sequentially during the polymerization, especially using an organic solvent with a boiling point of greater than or equal to 60° C., for instance isododecane, ethanol, ethyl acetate, tetrahydrofuran, methyltetrahydrofuran or methyl ethyl ketone. The organic solvent makes it possible to dissolve the monomers used and the polymer formed.

The polymerization is especially performed in the presence of a radical initiator especially of peroxide type (for example tert-butyl peroxy-2-ethylhexanoate: Trigonox 21S; 2,5-dimethyl-2,5-bis(2-ethylhexanoylperoxy)hexane: Trigonox 141; tert-butyl peroxypivalate: Trigonox 25C75 from AkzoNobel) or of azo type, for example (AIBN: azobisisobutyronitrile; V50: 2,2'-azobis(2-amidinopropane) dihydrochloride).

The polymerization may be performed at a temperature ranging from 60 to 100° C., and preferably ranging from 60 to 85° C.

The polymerization time may be about 24 hours.

A subject of the invention is also the novel polymers derived from the polymerization of:
(a) 45% to 94.5% by weight, relative to the total weight of monomers, of linear or branched $C_8$-$C_{22}$ alkyl (meth) acrylate;
(b) 5% to 25% by weight of maleic anhydride monomer;
(c) 0.5% to 50% by weight of additional monomer chosen from:
   (i) polydimethylsiloxane silicone monomers bearing a mono(meth)acryloyloxy end group as defined previously;
   (ii) linear or branched $C_1$-$C_6$ alkyl (meth)acrylate or $C_6$-$C_{12}$ cycloalkyl (meth)acrylate non-silicone monomers;
and also similar polymers with the following preferred contents:
(a) 75% to 95% and (b) 5% to 25%; (a) 75% to 90% and (b) 10% to 25%; (a) 78% to 87% and (b) 13% to 22%;
(a) 45% to 94.5% and (b) 5% to 25% and (c) 0.5% to 50%; (a) 45% to 90% and (b) 5% to 25% and (c) 5% to 50%; (a) 50% to 75% and (b) 10% to 25% and (c) 15% to 40%; (a) 52% to 67% and (b) 13% to 22% and (c) 20% to 35%.

A subject of the invention is also the novel polymers described previously as second, third and fourth embodiments.

A subject of the invention is also the novel polymers derived from the polymerization of:
(a) 45% to 95% by weight, relative to the total weight of monomers, of an ethylenic monomer bearing an at least $C_8$ linear or branched alkyl group chosen from:
   i) the (meth)acrylamides of formula $CH_2=C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group;
   ii) the vinyl esters of formula $R_5$—O—CH—CH=$CH_2$ in which $R_5$ represents a linear or branched $C_8$-$C_{22}$ alkyl group;
   iii) the ethers of formula $R_6$—O—CH=$CH_2$ in which $R_6$ represents a linear or branched $C_8$-$C_{22}$ alkyl group;
(b) 5% to 25% by weight of maleic anhydride monomer;
(c) 0% to 50% by weight of additional monomer chosen from:
   (i) linear or branched $C_1$-$C_6$ alkyl (meth)acrylate or $C_6$-$C_{12}$ cycloalkyl (meth)acrylate non-silicone monomers; or
   (ii) polydimethylsiloxane silicone monomers bearing a mono(meth)acryloyloxy end group as defined previously;
and also similar polymers with the following preferred contents:
a) 75% to 95% and (b) 5% to 25%; (a) 75% to 90% and (b) 10% to 25%; (a) 78% to 87% and (b) 13% to 22%;
(a) 45% to 94.5% and (b) 5% to 25% and (c) 0.5% to 50%;
(a) 45% to 90% and (b) 5% to 25% and (c) 5% to 50%; (a) 50% to 75% and (b) 10% to 25% and (c) 15% to 40%; (a) 52% to 67% and (b) 13% to 22% and (c) 20% to 35%.

The ethylenic polymer may be present in a composition comprising a physiologically acceptable medium, in particular in a cosmetic composition.

The term "physiologically acceptable medium" means a medium that is compatible with human keratin materials and in particular with the skin.

The term "cosmetic composition" is understood to mean a composition that is compatible with keratin materials, which has a pleasant colour, odour and feel and which does not cause unacceptable discomfort (stinging, tautness or redness) liable to discourage the consumer from using it.

The ethylenic polymer as defined previously may be present in the composition used according to the invention in a content ranging from 0.1% to 40% by weight, relative to the total weight of the composition, preferably from 0.5% to 35% by weight of active material, preferentially ranging from 1% to 30% by weight, and more preferentially ranging from 10% to 30% by weight.

The composition used according to the invention is generally suitable for topical application to keratin materials, and thus generally comprises a physiologically acceptable medium, i.e. a medium that is compatible with the skin and/or its integuments. It is preferably a cosmetically acceptable medium, i.e. a medium which has a pleasant colour, odour and feel and which does not cause any unacceptable discomfort (stinging, tautness or redness) liable to discourage the consumer from using this composition.

The amine compound used in the process according to the invention is especially an amine compound chosen from polyamine compounds bearing several primary amine and/or secondary amine groups or alternatively amino alkoxysilanes. It may thus be chosen from amino alkoxysilane compounds, diamine compounds and triamine compounds.

According to a first embodiment of the invention, the polyamine compound is a compound comprising from 2 to 20 carbon atoms, in particular a non-polymeric compound. The term "non-polymeric compound" means a compound which is not directly obtained via a monomer polymerization reaction Polyamine compounds that may be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis (3-aminopropylamino)ethane, N,N'-bis(3-aminopropyl)-1, 3-propanediamine, ethylenediamine, 1,3-propylenediamine, 1,4-butylenediamine, lysine, cystamine, xylenediamine, tris (2-aminoethyl)amine and spermidine. Preferably, the polyamine compound is chosen from ethylenediamine, 1,3-propylenediamine and 1,4-butylenediamine. Preferentially, the polyamine compound is ethylenediamine.

The amine compound may also be chosen from amino alkoxysilanes, such as those of formula (II):

in which:
$R'_1$ is a linear or branched, saturated or unsaturated, cyclic or acyclic $C_1$-$C_6$ hydrocarbon-based chain substituted with a group chosen from the following groups:
amine $NH_2$ or $NHR$ with $R=C_1$-$C_4$ alkyl,
an aryl or aryloxy group substituted with an amino group or with a $C_1$-$C_4$ aminoalkyl group,
$R'_1$ possibly being interrupted in its chain with a heteroatom (O, S, NH) or a carbonyl group (CO), $R'_1$ being linked to the silicon atom directly via a carbon atom, R'$_2$ and R'$_3$, which may be identical or different, represent a linear or branched alkyl group comprising from 1 to 6 carbon atoms, z denotes an integer ranging from 1 to 3, and x denotes an integer ranging from 0 to 2, with z+x=3.

Preferably, R'$_2$ represents an alkyl group comprising from 1 to 4 carbon atoms.

Preferably, R'$_2$ represents a linear alkyl group, comprising from 1 to 4 carbon atoms.

Preferably, R'$_2$ represents an ethyl group.

Preferably, R'$_3$ represents an alkyl group comprising from 1 to 4 carbon atoms.

Preferably, R'$_3$ represents a linear alkyl group, comprising from 1 to 4 carbon atoms.

Preferably, R'$_3$ represents a methyl or ethyl group.

Preferably, R'$_1$ is an acyclic chain.

Preferably, R'$_1$ is a linear or branched, saturated or unsaturated $C_1$-$C_6$ hydrocarbon-based chain, substituted with an amine group NH$_2$ or NHR (R=$C_1$-$C_6$ alkyl, $C_3$-$C_6$ cycloalkyl or $C_6$ aromatic). Preferentially, R'$_1$ is a saturated linear $C_1$-$C_6$ hydrocarbon-based chain substituted with an amine group NH$_2$. More preferentially, R'$_1$ is a saturated linear $C_2$-$C_4$ hydrocarbon-based chain substituted with an amine group NH$_2$.

Preferably, R'$_1$ is a saturated linear $C_1$-$C_6$ hydrocarbon-based chain substituted with an amine group NH$_2$.

R'$_2$ represents an alkyl group comprising from 1 to 4 carbon atoms,

R'$_3$ represents an alkyl group comprising from 1 to 4 carbon atoms,

Preferably, z is equal to 3.

Preferably, the amino alkoxysilane of formula (II) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.

Preferably, the amino alkoxysilane (II) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the amino alkoxysilane (II) is 3-aminopropyltriethoxysilane (APTES).

Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine and lysine.

Preferentially, the amine compound is chosen from ethylenediamine, 1,3-propylenediamine, 1,4-butylenediamine and 3-aminopropyltriethoxysilane (APTES). More preferentially, the amine compound is ethylenediamine or 3-aminopropyltriethoxysilane (APTES).

The amine compound may also be chosen from amine-based polymers, in particular having a weight-average molecular weight ranging from 500 to 1 000 000, preferably ranging from 500 to 500 000, and preferentially ranging from 500 to 100 000.

As amine-based polymer, use may be made of poly(($C_2$-$C_5$)alkyleneimines), and in particular polyethyleneimines and polypropyleneimines, especially poly(ethyleneimine)s (for example the product sold under the reference 46,852-3 by the company Aldrich Chemical); poly(allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing NH$_2$ groups, such as polylysine, for example the product sold by the company JNC Corporation (formerly Chisso); aminodextran, such as the product sold by the company CarboMer Inc; amino polyvinyl alcohol, such as the product sold by the company CarboMer Inc, acrylamidopropylamine-based copolymers; chitosans; polydimethylsiloxanes comprising primary amine groups at the chain end or on side chains, for example aminopropyl side or end groups, for instance those of formula (A) or (B) or (C):

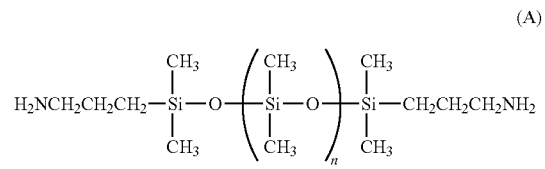

(A)

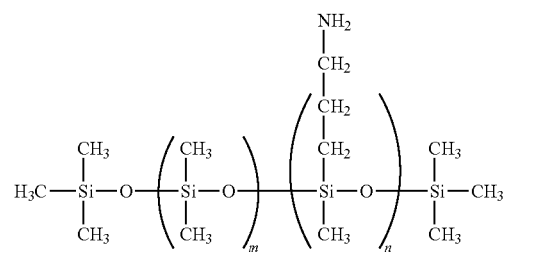

(B)

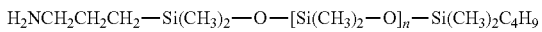

(C)

in formula (A): the value of n is such that the weight-average molecular weight of the silicone is between 500 and 55 000. As an example of aminosilicone (A), mention may be made of those sold under the names DMS-A11, DMS-A12, DMS-A15, DMS-A21, DMS-A31, DMS-A32 and DMS-A35 by the company Gelest;

in formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest;

in formula (C), the value of n is such that the weight-average molecular weight of the silicone is between 500 and 3000. As an example of silicone (C), mention may be made of those sold under the names MCR-A11 and MCR-A12 by the company Gelest;

amodimethicones of formula (D):

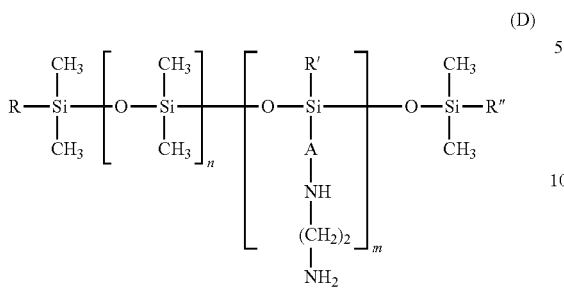

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000 approximately;

the amodimethicones of formula (K):

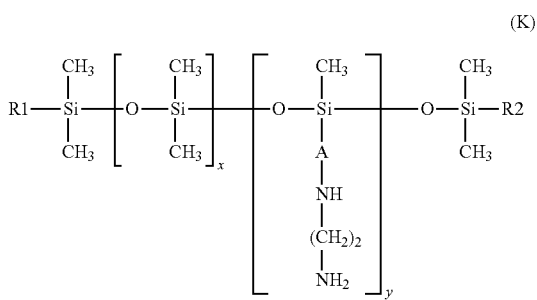

in which:
R1 and R2, which may be identical or different, preferably identical, represent a linear or branched, saturated or unsaturated alkyl group comprising from 6 to 30 carbon atoms, preferably from 8 to 24 carbon atoms and preferentially from 12 to 20 carbon atoms,
A represents a linear or branched alkylene radical group containing from 2 to 8 carbon atoms,
x and y are numbers ranging from 1 to 5000; preferably, x ranges from 10 to 2000 and especially from 100 to 1000; preferably, y ranges from 1 to 100.

Preferably, A comprises from 3 to 6 carbon atoms, in particular 4 carbon atoms; preferably, A is branched. A may be a divalent radical chosen from: —$CH_2CH_2CH_2$— and —$CH_2CH(CH_3)CH_2$—.

Preferably, R1 and R2, which may be identical or different, represent a saturated linear alkyl group comprising from 6 to 30 carbon atoms, preferentially from 8 to 24 carbon atoms and especially from 12 to 20 carbon atoms, for instance a dodecyl, tetradecyl, pentadecyl, hexadecyl, heptadecyl, octadecyl, nonadecyl or eicosyl group. Advantageously, R1 and R2 represent a mixture of hexadecyl (cetyl) and octadecyl (stearyl) radicals (mixture also known as cetearyl).

Preferentially, for the amodimethicone of formula (K):
x ranges from 10 to 2000 and especially from 100 to 1000;
y ranges from 1 to 100;
A comprises from 3 to 6 carbon atoms, and in particular 4 carbon atoms; preferably, A is branched; preferentially, A is chosen from the divalent radicals: —$CH_2CH_2CH_2$— and —$CH_2CH(CH_3)CH_2$—; and R1 and R2, which may be identical or different, represent a saturated linear radical comprising from 6 to 30 carbon atoms, preferably from 8 to 24 carbon atoms and especially from 12 to 20 carbon atoms, for instance a dodecyl, tetradecyl, pentadecyl, hexadecyl, heptadecyl, octadecyl, nonadecyl or eicosyl group. Advantageously, R1 and R2 represent a mixture of hexadecyl (cetyl) and octadecyl (stearyl) radicals (mixture also known as cetearyl).

As amodimethicone of formula (K), use may be made of bis-cetearyl amodimethicone (INCI name), especially the product sold under the name Silsoft® AX by the company Momentive Performance Materials.

The polyether amines known especially under the reference Jeffamine® from the company Huntsman; and especially:

Polyethylene glycol and/or polypropylene glycol α,ω-diamines (bearing an amine function at the end of the chain), which may comprise from 2 to 80 units derived from propylene oxide, or which may comprise from 2 to 50 units derived from ethylene oxide and from 1 to 10 units derived from propylene oxide, for instance the products sold under the names Jeffamine® D-230, D-400, D-2000, D-4000, ED-600, ED-9000, ED-2003;

Polytetrahydrofuran (or polytetramethylene glycol) α,ω-diamines;

polybutadiene α,ω-diamines;

Polyamidoamine (PANAM) dendrimers bearing amine end functions;

Poly(meth)acrylates or poly(meth)acrylamides bearing primary or secondary amine side functions, such as poly(3-aminopropyl)methacrylamide or poly(2-aminoethyl) methacrylate.

As amine-based polymer, use is preferably made of polydimethylsiloxanes comprising primary amine groups at the chain end or on side chains.

Preferentially, polydimethylsiloxanes comprising aminopropyl end groups at the chain end are used.

Advantageously, the polyamine compounds used in the process according to the invention are chosen from polydimethylsiloxanes comprising primary amine groups at the chain end or on side chains, amodimethicones of formula (K), in particular bis-cetearyl amodimethicone; polyethylene glycol and/or polypropylene glycol α,ω-diamines; ethylenediamine, 1,3-propylenediamine, 1,4-butylenediamine, preferably ethylenediamine.

Preferentially, the amine compounds used in the process according to the invention are chosen from polydimethylsiloxanes comprising aminopropyl end groups at the chain end, bis-cetearyl amodimethicone, polyethylene glycol/polypropylene glycol α,ω-diamine copolymers comprising from 2 to 50 units derived from ethylene oxide and from 1 to 10 units derived from propylene oxide, 3-aminopropyltriethoxysilane (APTES).

When the compound is an amino alkoxysilane, the composition containing it is anhydrous.

The composition containing the ethylenic polymer, when it is intended to be mixed with the composition containing the amino alkoxysilane, is also anhydrous.

When the polyamine compound is silicone-based, the film obtained via the process according to the invention has good gloss properties.

Advantageously, the amine compound used in the process according to the invention is used in a mole ratio of amine group of the amine compound/maleic anhydride group of the ethylenic polymer ranging from 0.01 to 10, preferably ranging from 0.1 to 5, preferentially ranging from 0.1 to 2 and more preferentially ranging from 0.1 to 1.

On contact with the ethylenic polymer, the polyamine compound reacts with the maleic anhydride functions to form a crosslinked polymer, for example in the following manner:

Scheme I

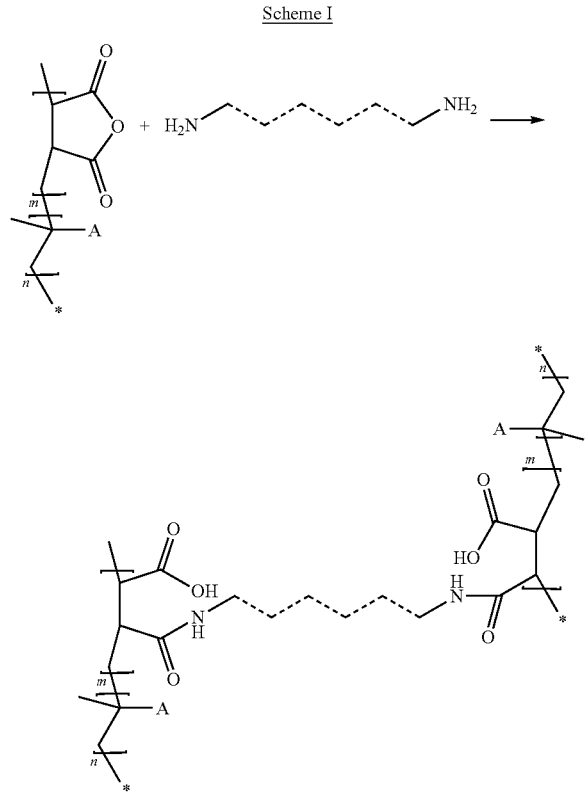

the unit bearing the group A symbolizing the unit derived from the fatty-chain ethylenic monomer.

Such a crosslinked polymer is novel and thus also forms the subject of the present invention.

The crosslinked polymer may thus be obtained by reacting said polyamine compound with the maleic anhydride acrylic polymer described previously. Some or all of the anhydride groups react with the NH or $NH_2$ group of the amine compound and form a unit bearing an amide group and a carboxylic acid group as described in scheme I.

The amino alkoxysilane (II) used in anhydrous medium reacts with the maleic anhydride group present in the polymer to form a unit having the following formula:

Scheme II

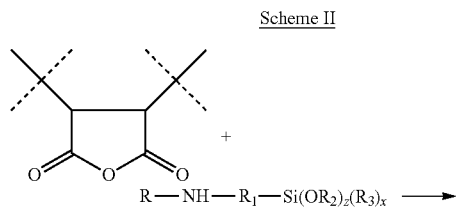

-continued

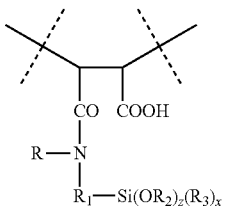

Amide and carboxylic acid unit

Such a polymer bearing an amino alkoxysilane group is novel and thus also forms the subject of the present invention. A subject of the invention is also an anhydrous composition comprising such a polymer bearing an amino alkoxysilane group and a physiologically acceptable medium.

The polymer bearing an amino alkoxysilane group may thus be obtained by reacting in anhydrous medium the amino alkoxysilane (II) with the maleic anhydride ethylenic polymer described previously. Some or all of the anhydride groups react with the NH group of compound (II) and form a unit bearing an amide group and a carboxylic acid group as described in scheme II.

A subject of the invention is thus the polymer obtained by reacting said amine compound with said maleic anhydride ethylenic polymer, the reaction being performed in anhydrous medium when the amine compound is an amino alkoxysilane.

A subject of the invention is also a composition comprising said polymer in a physiologically acceptable medium.

According to one embodiment of the process according to the invention, a mixture, especially an extemporaneous mixture, of the ethylenic polymer and of an amino alkoxysilane (II) is prepared and the mixture is applied to the keratin materials. It is also possible to perform sequential application of, on the one hand, the ethylenic polymer and, on the other hand, an amino alkoxysilane (II) as are defined previously.

Advantageously, the process according to the invention is performed under ambient conditions, in particular at an ambient temperature that may range from 15° C. to 30° C., preferably ranging from 18° C. to 25° C.

According to a preferred embodiment of the invention, the composition comprising the ethylenic polymer may contain a hydrocarbon-based oil. More generally, the compositions used in the process according to the invention preferably comprise an oil, especially a hydrocarbon-based oil.

The hydrocarbon-based oil is an oil that is liquid at room temperature (25° C.).

The term "hydrocarbon-based oil" means an oil formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be volatile or non-volatile.

The hydrocarbon-based oil may be chosen from:
hydrocarbon-based oils containing from 8 to 14 carbon atoms, and especially:
branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade name Isopar or Permethyl, linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides constituted of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, *quinoa* oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers having from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular branched, hydrocarbon-based chain containing from 1 to 40 carbon atoms, on the condition that $R_1+R_2$ 10, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 14 carbon atoms, in particular the apolar oils described previously.

Preferentially, the hydrocarbon-based oil is isododecane.

The composition comprising the polymer may contain, in addition to the hydrocarbon-based oil, a silicone oil. The term "silicone oil" means an oil comprising at least one silicon atom and especially at least one Si—O group. The silicone oil may be volatile or non-volatile.

The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1300 Pa (0.01 to 10 mmHg).

The term "non-volatile oil" means an oil with a vapour pressure of less than 0.13 Pa.

Volatile silicone oils that may be mentioned include volatile linear or cyclic silicone oils, especially those with a viscosity 8 centistokes (cSt) ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes comprising alkyl, alkoxy or phenyl groups, which are pendant or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Advantageously, the composition may comprise a hydrocarbon-based oil in a content ranging from 60% to 100% by weight relative to the total weight of the oils present in the composition and from 0 to 40% by weight of silicone oil. According to a preferred embodiment of the invention, the composition contains as oil only a hydrocarbon-based oil.

The composition according to the invention may comprise a cosmetic additive chosen from water, fragrances, preserving agents, fillers, UV-screening agents, oils, waxes, surfactants, moisturizers, vitamins, ceramides, antioxidants, free-radical scavengers, polymers, thickeners and dyestuffs.

The composition according to the invention may also comprise a dyestuff such as pulverulent dyestuffs, liposoluble dyes or water-soluble dyes. This dyestuff may be present in a content ranging from 0.01% to 30% by weight, relative to the total weight of the composition.

The pulverulent dyestuffs may be chosen from pigments and nacres.

The pigments may be white or coloured, mineral and/or organic, and coated or uncoated. Among the mineral pigments that may be mentioned are titanium dioxide, optionally surface-treated, zirconium, zinc or cerium oxides, and also iron or chromium oxides, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

Needless to say, those skilled in the art will take care to select this or these optional additional compound(s), and/or the amount thereof, such that the anti-wrinkle properties of the composition according to the invention are not, or are not substantially, adversely affected by the envisaged addition.

Advantageously, the composition according to the invention is a skincare composition.

The composition according to the invention may be a makeup composition such as a foundation, a lipstick or a liner.

According to one embodiment, the composition according to the invention is a makeup composition and comprises a volatile oil and a non-volatile oil as described previously. In particular, the makeup composition may comprise a hydrocarbon-based volatile oil and a hydrocarbon-based non-volatile oil.

According to one embodiment, the composition according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

In particular, when the process according to the invention uses an amino alkoxysilane as described previously, the composition(s) used are advantageously anhydrous.

The invention is illustrated in greater detail in the examples that follow.

EXAMPLE 1

2-Ethylhexyl Acrylate/Maleic Anhydride Copolymer (85/15 by Weight)

170 g of 2-ethylhexyl acrylate and 30 g of maleic anhydride were placed in a jacketed 1-litre reactor equipped with a stirring anchor. A mixture of 210 g of isododecane and 90 g of ethyl acetate was then added.

The medium was brought to a temperature of 40° C. with stirring (150 rpm) and was sparged with argon for 10 minutes, followed by addition of 2 g of initiator tert-butyl peroxy-2-ethylhexanoate (Trigonox® 21S from AkzoNobel).

The heating of the jacket was set at 90° C. for 7 hours at 150 rpm.

The medium was then diluted with 300 g of isododecane, and then concentrated by distillation to remove the ethyl acetate and the unreacted maleic anhydride.

A solution containing 30% by weight of the copolymer in isododecane was finally obtained.

The polymer obtained has a molecular weight (Mw) of close to 12 000 g/mol.

EXAMPLE 2

2-Ethylhexyl Acrylate/Maleic Anhydride Copolymer (80/20 by Weight)

The polymer was prepared according to the procedure of Example 1, using 160 g of 2-ethylhexyl acrylate and 40 g of maleic anhydride.

A solution containing 32% by weight of the copolymer in isododecane (yield of greater than 90%) was finally obtained.

The polymer obtained has a molecular weight (Mw) of close to 15000 g/mol.

EXAMPLE 3

2-Ethylhexyl Acrylate/PDMS Methacrylate*/Maleic Anhydride Copolymer (50/30/20 by Weight)

The polymer was prepared according to the procedure of Example 1, using:
40 g of maleic anhydride with 28 g of isododecane and 21 g of ethyl acetate;
sparging with argon, followed by addition over 1 hour of a mixture of 100 g of 2-ethylhexyl acrylate, 60 g of PDMS methacrylate* (X-22-2426 from Shin-Etsu; size of the PDMS chain=12 000 g/mol), 168 g of isododecane, 72 g of ethyl acetate and 2 g of Trigonox® 21S.

A solution containing 40% by weight of the copolymer in isododecane was finally obtained.

EXAMPLE 4

2-Ethylhexyl Acrylate/Stearyl Acrylate/Maleic Anhydride Copolymer (50/30/20 by Weight)

The polymer was prepared according to the procedure of Example 1, using:
20 g of 2-ethylhexyl acrylate and 20 g of maleic anhydride;
40 g of maleic anhydride with 28 g of isododecane and 21 g of ethyl acetate; sparging with argon, followed by addition over 1 hour of a mixture of 100 g of 2-ethylhexyl acrylate, 60 g of stearyl methacrylate, 168 g of isododecane, 72 g of ethyl acetate and 2 g of Trigonox® 21S.

A solution containing 41% by weight of the copolymer in isododecane was finally obtained.

The polymer obtained has a molecular weight (Mw) of close to 17 000 g/mol.

COMPARATIVE EXAMPLES 5 TO 10

Cosmetic Evaluation of Makeup Compositions with Application in Two Steps

The three makeup compositions (lip gloss) of base coat containing the polymer of Example 1 or of Example 2 and a top coat composition containing APTES described below were prepared.

Each base coat composition was applied onto a skin equivalent support made of elastomer by producing a deposit with a wet thickness of 100 μm, which was left to dry at room temperature (25° C.) for 24 hours.

The top coat composition was then applied onto each dry base coat deposit by producing a deposit with a wet thickness of 100 μm, which was left to dry at room temperature (25° C.) for 24 hours.

The state of the film obtained before (outside the invention) and after (invention) applying the top coat composition was then observed.

The elastomer support was also deformed manually and the state of the film after this deformation was observed to determine its resistance to deformation.

The strength of the film obtained was evaluated by separately applying 0.5 ml of water, 0.5 ml of olive oil and 0.5 ml of sebum; after 5 minutes of contact, the surface of the film was rubbed with cotton wool and the state of the film was then observed (degraded or undegraded appearance of the film).

The tackiness of the film and its capacity for transferring or not transferring on touching the film with a finger were also evaluated.

The evaluation was made in the following manner:

+++: very efficient evaluated cosmetic property
++: moderately efficient evaluated cosmetic property
+: sparingly efficient evaluated cosmetic property
0: inefficient evaluated cosmetic property The following results were obtained:

|  | Example 5 | Example 6 (invention) | Example 7 | Example 8 (invention) |
|---|---|---|---|---|
| Polymer of Example 1 | 25 g AM | 25 g AM | — | — |
| Polymer of Example 2 | — | — | 20 g AM | 20 g AM |
| Pigmentary paste containing 40% by weight of pigment in isododecane | 5 g with DC Red 7 | 5 g with DC Red 7 | 5 g with DC Red 7 | 5 g with DC Red 7 |
| Disteardimonium hectorite (Bentone Gel ISD V from Elementis) | 10 g | 10 g | 10 g | 10 g |
| 2-Octyldodecanol |  |  | 20 g | 20 g |
| Isododecane | qs 100 g | qs 100 g | qs 100 g | qs 100 g |
| APTES |  | 5 g |  | 5 g |
| Isododecane |  | 95 g |  | 95 g |
| Evaluation of the film |  |  |  |  |
| Appearance of the film | Homogeneous film | Homogeneous film | Homogeneous film | Homogeneous film |
| Resistance to deformation | Yes without damaging the film | Yes without damaging the film | Yes without damaging the film | Yes without damaging the film |
| Water resistance | ++ | +++ | ++ | +++ |
| Olive oil resistance | 0 | +++ | 0 | +++ |
| Sebum resistance | 0 | +++ | 0 | +++ |
| Non-tacky | 0 | +++ | 0 | +++ |
| Transfer-resistant | 0 | +++ | 0 | +++ |

|  | Example 9 | Example 10 (invention) |
|---|---|---|
| Polymer of Example 1 | 25 g AM | 25 g AM |
| Pigmentary paste containing 40% by weight of pigment in isododecane | 5 g with red iron oxide | 5 g with red iron oxide |
| Disteardimonium hectorite (Bentone Gel ISD V from Elementis) | 10 g | 10 g |
| Isododecane | 65 g | 65 g |
| APTES |  | 15 g |
| Isododecane |  | 95 g |
| Evaluation of the film |  |  |
| Appearance of the film | Homogeneous film | Homogeneous film |
| Resistance to deformation | Yes without damaging the film | Yes without damaging the film |
| Water resistance | ++ | +++ |
| Olive oil resistance | 0 | +++ |
| Sebum resistance | 0 | +++ |
| Non-tacky | + | +++ |
| Transfer-resistant | 0 | +++ |

The results obtained show that the deposits resulting from the application of polymer 1 followed by APTES (Examples 6, 10) and those resulting from the application of polymer 2 with 2-octyldodecanol (Example 8) form a non-tacky homogeneous film that does not transfer to the finger, and that is resistant to deformation, to water, to oil and to sebum, whereas the sole application of polymer 1 (Examples 5, 9) or of polymer 2 (Example 7) forms a deposit that is much more tacky and that transfers onto the finger and has poor resistance to oil and to sebum.

Thus, the non-tacky and transfer-resistant aspect on contact with the finger, and also the resistance of the film on contact with olive oil and sebum are markedly improved with the application of the top coat composition containing APTES.

The lipstick compositions of Examples 6 or 8 or 10 applied to the lips thus make it possible to obtain a non-tacky, transfer-resistant and oil- and sebum-resistant makeup which thus has good staying power.

COMPARATIVE EXAMPLES 11 TO 14

Cosmetic Evaluation of Makeup Compositions with Application in One Step

The makeup compositions (lip gloss) described below containing the polymer of Example 2 with or without APTES were prepared, and the composition was then applied onto a skin equivalent support made of elastomer by producing a deposit with a wet thickness of 100 μm, which was left to dry at room temperature (25° C.) for 24 hours.

The cosmetic properties of the film obtained were evaluated according to the tests described previously in Examples 5 to 10.

The following results were obtained:

The results obtained show that the deposit resulting from the application of polymer 2 mixed with APTES, with or without 2-octyldodecanol (Examples 12, 14) forms a non-tacky homogeneous film that does not transfer to the finger, and that is resistant to water, to oil and to sebum, whereas the sole application of polymer 2, with or without 2-octyldodecanol (Examples 11, 13) forms a deposit that is much more tacky and that transfers onto the finger and has poor resistance to oil and to sebum.

Thus, the non-tacky and transfer-resistant aspect on contact of the finger with the film, and also the resistance of the film on contact with olive oil and sebum, are markedly improved with the application of the composition containing the polymer of Example 2 and APTES.

The lipstick composition (Examples 12, 14) applied to the lips thus makes it possible to obtain a non-tacky, transfer-resistant and water-, oil- and sebum-resistant makeup which thus has good staying power.

COMPARATIVE EXAMPLES 15 TO 20

Cosmetic Evaluation of Makeup Compositions with Application in One Step

The makeup compositions (lip gloss; foundation) described below containing the polymer of Example 2 with or without APTES were prepared, and the composition was then applied onto a skin equivalent support made of elastomer by producing a deposit with a wet thickness of 100 μm, which was left to dry at room temperature (25° C.) for 24 hours.

The cosmetic properties of the film obtained were evaluated according to the tests described previously in Examples 5 to 10.

|  | Example 11 | Example 12 (invention) | Example 13 | Example 14 (invention) |
|---|---|---|---|---|
| Composition |  |  |  |  |
| Polymer of Example 1 | 20 g AM | 20 g AM | 20 g AM | 20 g AM |
| Pigmentary paste containing 40% by weight of pigment in isododecane | 5 g with DC Red 7 | 5 g with DC Red 7 | 5 g with DC Red 7 | 5 g with DC Red 7 |
| Disteardimonium hectorite (Bentone Gel ISD V from Elementis) | 10 g | 10 g | 10 g | 10 g |
| APTES | — | 5 g | — | 5 g |
| 2-Octyldodecanol | — | — | 20 g | 20 g |
| Isododecane | 65 g | 60 g | 45 g | 60 g |
| Evaluation of the film |  |  |  |  |
| Appearance of the film | Homogeneous film | Homogeneous film | Homogeneous film | Homogeneous film |
| Resistance to deformation | Yes without damaging the film | Yes but with fragmentation of the film | Yes without damaging the film | Yes without damaging the film |
| Water resistance | ++ | +++ | ++ | +++ |
| Olive oil resistance | 0 | +++ | 0 | +++ |
| Sebum resistance | 0 | +++ | 0 | +++ |
| Non-tacky | 0 | +++ | 0 | +++ |
| Transfer-resistant | 0 | +++ | 0 | +++ |

The following results were obtained:

|  | Example 15 | Example 16 | Example 17 | Example 18 | Example 19 | Example 20 |
|---|---|---|---|---|---|---|
| Polymer of Example 2 | 20 g | 20 g | 25 g | 25 g | 20 g | 20 g |
| Pigmentary paste containing 40% by weight of pigment in isododecane | 5 g with DC Red 7 | 5 g with DC Red 7 | 5 g with DC Red 7 | 5 g with DC Red 7 | 5 g with red iron oxide | 5 g with red iron oxide |
| APTES | — | 5 g | — | 5 g | — | 5 g |
| Isododecane | 75 g | 70 g | 70 g | 65 g | 75 g | 70 g |
| Appearance of the film | Homogeneous film | Homogeneous film | Homogeneous film | Homogeneous film | Homogeneous film | Homogeneous film |
| Resistance to deformation | Yes without damaging the film | Yes without damaging the film | Yes without damaging the film | Yes without damaging the film | Yes without damaging the film | Yes without damaging the film |
| Water resistance | ++ | +++ | ++ | +++ | ++ | +++ |
| Olive oil resistance | 0 | +++ | 0 | +++ | 0 | +++ |
| Sebum resistance | 0 | +++ | 0 | +++ | 0 | +++ |
| Non-tacky | 0 | +++ | 0 | +++ | 0 | +++ |
| Transfer-resistant | 0 | +++ | 0 | +++ | 0 | +++ |

The results obtained show that the deposit resulting from the application of polymer 2 mixed with APTES, with or without 2-octyldodecanol (Examples 16, 18, 20) forms a non-tacky homogeneous film that does not transfer to the finger, and that is resistant to water, to oil and to sebum, whereas the sole application of polymer 2, with or without 2-octyldodecanol (Examples 15, 17, 19) forms a deposit that is much more tacky and that transfers onto the finger and has poor resistance to oil and to sebum.

Thus, the non-tacky and transfer-resistant aspect on contact of the finger with the film, and also the resistance of the film on contact with water, olive oil and sebum, are markedly improved with the application of the composition containing the polymer of Example 2 and APTES.

The lipstick composition (Examples 16, 18) applied to the lips thus makes it possible to obtain a non-tacky, transfer-resistant and oil- and sebum-resistant makeup which thus has good staying power.

The composition of Example 20 applied to the skin thus makes it possible to obtain a non-tacky, transfer-resistant and water-, oil- and sebum-resistant makeup which thus has good staying power.

COMPARATIVE EXAMPLES 21 TO 23

Cosmetic Evaluation of Makeup Compositions with Application in Two Steps

The three makeup compositions (lip gloss) of base coat containing the polymer of Example 1 and a top coat composition containing 3-aminopropyl-terminated polydimethylsiloxane described below were prepared.

The compositions were applied and the cosmetic properties of the film obtained were evaluated as described previously in Examples 5 to 10.

The following results were obtained:

|  | Example 5 | Example 21 (invention) | Example 22 | Example 23 (invention) |
|---|---|---|---|---|
| Polymer of Example 1 | 25 g AM | 25 g AM | 20 g AM | 20 g AM |
| Pigmentary paste containing 40% by weight of pigment in isododecane | 5 g with DC Red 7 | 5 g with DC Red 7 | 5 g with DC Red 7 | 5 g with DC Red 7 |
| Disteardimonium hectorite (Bentone Gel ISD V from Elementis) | 10 g | 10 g | 10 g | 10 g |
| 2-Octyldodecanol |  |  | 20 g | 20 g |
| Isododecane | qs 100 g | qs 100 g | qs 100 g | qs 100 g |
| 3-Aminopropyl-terminated polydimethylsiloxane (Mn 2 500; reference 481688 from Sigma) |  | 5 g |  | 5 g |
| Isododecane |  | 95 g |  | 95 g |
| Evaluation of the film |  |  |  |  |
| Appearance of the film | Homogeneous film | Homogeneous film | Homogeneous film | Homogeneous film |

|  | Example 5 | Example 21 (invention) | Example 22 | Example 23 (invention) |
|---|---|---|---|---|
| Resistance to deformation | Yes without damaging the film | Yes without damaging the film | Yes without damaging the film | Yes without damaging the film |
| Water resistance | ++ | +++ | ++ | +++ |
| Olive oil resistance | 0 | +++ | 0 | +++ |
| Sebum resistance | 0 | +++ | 0 | +++ |
| Non-tacky | 0 | +++ | 0 | +++ |
| Transfer-resistant | 0 | +++ | 0 | +++ |

The results obtained show that the deposits resulting from the application of polymer 1 followed by 3-aminopropyl-terminated polydimethylsiloxane (Example 21) with 2-octyldodecanol (Example 23) form a non-tacky homogeneous film that does not transfer to the finger, and that is resistant to deformation, to water, to oil and to sebum, whereas the sole application of polymer 1 (Examples 5, 22) forms a deposit that is much more tacky and that transfers onto the finger and has poor resistance to oil and to sebum.

Thus, the non-tacky and transfer-resistant aspect on contact with the finger, and also the resistance of the film on contact with water, olive oil and sebum are markedly improved with the application of the top coat composition containing 3-aminopropyl-terminated polydimethylsiloxane.

The lipstick compositions of Examples 21 or 23 applied to the lips thus make it possible to obtain a non-tacky, transfer-resistant and water-, oil- and sebum-resistant makeup which thus has good staying power.

COMPARATIVE EXAMPLES 24 AND 25

Cosmetic Evaluation of Makeup Compositions with Application in Two Steps

The 2 makeup compositions (lipstick) of base coat containing the polymer of Example 4 and a top coat composition containing 3-aminopropyl-terminated polydimethylsiloxane described below were prepared.

The compositions were applied and the cosmetic properties of the film obtained were evaluated as described previously in Examples 5 to 10.

The following results were obtained:

|  | Example 24 | Example 25 (invention) |
|---|---|---|
| Polymer of Example 4 | 20 g AM | 20 g AM |
| Pigmentary paste containing 40% by weight of pigment in isododecane | 8.6 g with DC Red 7 | 8.6 g with DC Red 7 |
| Microcrystalline wax (Microwax HW from Paramelt) | 15 g | 15 g |
| Hydrogenated polyisobutene (Parleam from Nippon Oil Fats) | 26 g | 26 g |
| Isododecane | qs 100 g | qs 100 g |
| 3-Aminopropyl-terminated polydimethylsiloxane (Mn 2 500; reference 481688 from Sigma) |  | 10 g |
| Microcrystalline wax (Microwax HW from Paramelt) |  | 15 g |
| Isododecane Evaluation of the film |  | qs 100 g |
| Appearance of the film | Homogeneous film | Homogeneous film |
| Resistance to deformation | Yes without damaging the film | Yes without damaging the film |
| Water resistance | ++ | +++ |
| Olive oil resistance | 0 | +++ |
| Sebum resistance | 0 | +++ |
| Non-tacky | + | +++ |
| Transfer-resistant | 0 | +++ |

The results obtained show that the deposit resulting from the application of polymer 4 followed by 3-aminopropyl-terminated polydimethylsiloxane (Example 25) forms a non-tacky homogeneous film that does not transfer to the finger, and that is resistant to deformation, to water, to oil and to sebum, whereas the sole application of polymer 4 (Example 24) forms a deposit that is much more tacky and that transfers onto the finger and has poor resistance to oil and to sebum.

Thus, the non-tacky and transfer-resistant aspect on contact with the finger, and also the resistance of the film on contact with water, olive oil and sebum are markedly improved with the application of the top coat composition containing 3-aminopropyl-terminated polydimethylsiloxane.

The lipstick compositions of Example 25 applied to the lips thus make it possible to obtain a non-tacky, transfer-resistant and water-, oil- and sebum-resistant makeup which thus has good staying power.

COMPARATIVE EXAMPLE 26

Cosmetic Evaluation of Makeup Compositions with Application in Two Steps

The two makeup compositions (foundation) of base coat containing the polymer of Example 1 and a top coat composition containing 3-aminopropyl-terminated polydimethylsiloxane described below were prepared.

The compositions were applied and the cosmetic properties of the film obtained were evaluated as described previously in Examples 5 to 10.

The following results were obtained:

|  | Example 9 | Example 26 (invention) |
|---|---|---|
| Base Coat | | |
| Polymer of Example 1 | 25 g AM | 25 g AM |
| Pigmentary paste containing 40% by weight of pigment in isododecane | 5 g with red iron oxide | 5 g with red iron oxide |
| Disteardimonium hectorite (Bentone Gel ISD V from Elementis) | 10 g | 10 g |
| Isododecane | qs 100 g | qs 100 g |
| Top Coat | | |
| 3-Aminopropyl-terminated polydimethylsiloxane (Mn 2 500; reference 481688 from Sigma) | | 10 g |
| Isododecane | | qs 100 g |
| Evaluation of the film | | |
| Appearance of the film | Homogeneous film | Homogeneous film |
| Resistance to deformation | Yes without damaging the film | Yes without damaging the film |
| Water resistance | ++ | +++ |
| Olive oil resistance | 0 | +++ |
| Sebum resistance | 0 | +++ |
| Non-tacky | + | +++ |
| Transfer-resistant | 0 | +++ |

The results obtained show that the deposit resulting from the application of polymer 1 followed by 3-aminopropyl-terminated polydimethylsiloxane (Example 26) forms a non-tacky homogeneous film that does not transfer to the finger, and that is resistant to deformation, to water, to oil and to sebum, whereas the sole application of polymer 1 (Example 9) forms a deposit that is much more tacky and that transfers onto the finger and has poor resistance to oil and to sebum.

Thus, the non-tacky and transfer-resistant aspect on contact with the finger, and also the resistance of the film on contact with water, olive oil and sebum are markedly improved with the application of the top coat composition containing 3-aminopropyl-terminated polydimethylsiloxane.

The compositions of Example 26 applied to the skin thus make it possible to obtain a non-tacky, transfer-resistant and water-, oil- and sebum-resistant makeup which thus has good staying power.

COMPARATIVE EXAMPLES 27 TO 33

Cosmetic Evaluation of Makeup Compositions with Application in Two Steps

The makeup composition (lipstick) of base coat containing the polymer of Example 2 and six top coat compositions containing an amine compound chosen from 3-aminopropyl-terminated polydimethylsiloxane (Mn=2500, 25 000 and 50 000), ethylenediamine, polyetherdiamine and bis-cetearyl amodimethicone described below were prepared.

The compositions were applied and the cosmetic properties of the film obtained were evaluated as described previously in Examples 5 to 10.

The glossy appearance of the film obtained was also evaluated in the same manner.

The following results were obtained:

|  | Example 27 | Example 28 (invention) | Example 29 (invention) | Example 30 (invention) | Example 31 (invention) | Example 32 (invention) | Example 33 (invention) |
|---|---|---|---|---|---|---|---|
| Base Coat | | | | | | | |
| Polymer of Example 2 | 20 g AM | 20 g AM | 20 g AM | 20 g AM | 20 g AM | 20 g AM | 20 g AM |
| Pigmentary paste containing 40% by weight of pigment in isododecane | 5 g with DC Red 7 | 5 g with DC Red 7 | 5 g with DC Red 7 | 5 g with DC Red 7 | 5 g with DC Red 7 | 5 g with DC Red 7 | 5 g with DC Red 7 |
| Disteardimonium hectorite (Bentone Gel ISD V from Elementis) | 10 g | 10 g | 10 g | 10 g | 10 g | 10 g | 10 g |
| Isododecane | qs 100 g | qs 100 g | qs 100 g | qs 100 g | qs 100 g | qs 100 g | qs 100 g |
| Top Coat | | | | | | | |
| 3-Aminopropyl-terminated polydimethylsiloxane (Mn 2 500; reference 481688 from Sigma) | | 10 g | | | | | |
| 3-Aminopropyl-terminated polydimethylsiloxane (Mn 25 000; DMS A-31 from Gelest) | | | 10 g | | | | |
| 3-Aminopropyl-terminated polydimethylsiloxane (Mn 50 000; DMS-A35 from Gelest) | | | | 10 g | | | |

-continued

|  | Example 27 | Example 28 (invention) | Example 29 (invention) | Example 30 (invention) | Example 31 (invention) | Example 32 (invention) | Example 33 (invention) |
|---|---|---|---|---|---|---|---|
| Ethylenediamine Polyetherdiamine (1) |  |  |  |  | 10 g | 10 g |  |
| Bis-cetearyl amodimethicone (2) |  |  |  |  |  |  | 10 g |
| Isododecane |  | qs 100 g | qs 100 g | qs 100 g | qs 100 g | qs 100 g | qs 100 g |
| Evaluation of the film |  |  |  |  |  |  |  |
| Appearance of the film | Homogeneous film | Homogeneous film | Homogeneous film | Homogeneous film | Homogeneous film | Homogeneous film | Homogeneous film |
| Resistance to deformation | Yes without damaging the film | Yes without damaging the film | Yes without damaging the film | Yes without damaging the film | Yes but film damaged | Yes without damaging the film | Yes without damaging the film |
| Olive oil resistance | 0 | +++ | +++ | +++ | +++ | +++ | +++ |
| Non-tacky | 0 | +++ | +++ | ++ | +++ | ++ | +++ |
| Transfer-resistant | 0 | +++ | +++ | +++ | +++ | ++ | +++ |
| Gloss | + | +++ | +++ | +++ | + | + | +++ |

(1) Jeffamine ® ED-900 Polyetheramine (Huntsman)
(2) Silsoft ® AX (Momentive Performance Materials)

The results obtained show that the deposit resulting from the application of polymer 2 followed by the amine compound (Examples 28 to 33) forms a non-tacky homogeneous film that does not transfer to the finger, and that is resistant to deformation and to oil, whereas the sole application of polymer 2 (Example 27) forms a deposit that is much more tacky and that transfers onto the finger and has poor resistance to oil.

Thus, the non-tacky and transfer-resistant aspect on contact with the finger, and also the resistance of the film on contact with olive oil are markedly improved with the application of the top coat composition containing the amine compounds tested. It is also noted that the aminosilicone compounds also afford good gloss to the film obtained.

The compositions of Examples 28 to 33 applied to the lips thus make it possible to obtain a non-tacky, transfer-resistant and oil-resistant makeup which thus has good staying power.

COMPARATIVE EXAMPLES 34 AND 35

Cosmetic Evaluation of Makeup Compositions with Application in Two Steps

The makeup composition (lipstick) of base coat containing the polymer of Example 3 and a top coat composition containing a 3-aminopropyl-terminated polydimethylsiloxane (Mn 50 000) were prepared.

The compositions were applied and the cosmetic properties of the film obtained were evaluated as described previously in Examples 5 to 10.

The glossy appearance of the film obtained was also evaluated in the same manner.

The following results were obtained:

|  | Example 34 | Example 35 (invention) |
|---|---|---|
| Base Coat |  |  |
| Polymer of Example 3 | 20 g AM | 20 g AM |
| Pigmentary paste containing 40% by weight of pigment in isododecane | 5 g with DC Red 7 | 5 g with DC Red 7 |
| Isododecane | qs 100 g | qs 100 g |
| Top Coat |  |  |
| 3-Aminopropyl-terminated polydimethylsiloxane (Mn 50 000) |  | 10 g |
| Isododecane |  | qs 100 g |
| Evaluation of the film |  |  |
| Appearance of the film | Homogeneous film | Homogeneous film |
| Resistance to deformation | Yes without damaging the film | Yes without damaging the film |
| Olive oil resistance | 0 | +++ |
| Non-tacky | + | +++ |
| Transfer-resistant | 0 | +++ |
| Sheen | + | +++ |

The results obtained show that the deposit resulting from the application of polymer 3 followed by 3-aminopropyl-terminated polydimethylsiloxane (Example 35) forms a non-tacky homogeneous film that does not transfer to the finger, and that is resistant to deformation and to oil, whereas the sole application of polymer 3 (Example 34) forms a deposit that is much more tacky and that transfers onto the finger and has poor resistance to oil.

Thus, the non-tacky and transfer-resistant aspect on contact with the finger, and also the resistance of the film on contact with olive oil are markedly improved with the application of the top coat composition containing 3-aminopropyl-terminated polydimethylsiloxane.

The lipstick compositions of Example 35 applied to the lips thus make it possible to obtain a non-tacky, transfer-resistant and oil-resistant makeup which thus has good staying power.

The invention claimed is:

1. A cosmetic process for treating keratin materials, comprising:
    either sequentially applying to the keratin materials 1) a composition comprising a maleic anhydride ethylenic polymer and 2) at least one amine component chosen from an amine compound chosen from polyamine compounds bearing several primary amine and/or secondary amine groups and amino alkoxysilanes, and a composition containing the amine compound and comprising a physiologically acceptable medium;
    or topically applying to the keratin materials a composition derived from mixing 1) a composition comprising a maleic anhydride ethylenic polymer and 2) at least one amine component chosen from an amine compound chosen from amino alkoxysilanes, and a composition containing the amine compound and comprising a physiologically acceptable medium;
    the ethylenic polymer being a random or gradient polymer derived from the polymerization of:
    (a) 45% to 95% by weight, relative to the total weight of monomers, of at least one ethylenic monomer bearing a $C_8$ to $C_{22}$ linear or branched alkyl group;
    (b) 5% to 25% by weight of maleic anhydride; and
    (c) 0 to 50% by weight of at least one additional monomer chosen from:
    (i) polydimethylsiloxane silicone monomers bearing a mono(meth)acryloyloxy end group of formula (I) below:

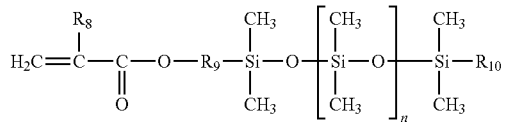

in which:
    $R_8$ denotes a hydrogen atom or a methyl group;
    $R_9$ denotes a linear or branched divalent hydrocarbon-based group containing from 1 to 10 carbon atoms and optionally containing one or two ether bonds —O—;
    $R_{10}$ denotes a linear or branched alkyl group containing from 1 to 10 carbon atoms; and
    n denotes an integer ranging from 1 to 300; and
    (ii) linear or branched $C_1$-$C_6$ alkyl (meth)acrylate or $C_6$-$C_{12}$ cycloalkyl (meth)acrylate non-silicone monomers;
    the compositions used being anhydrous when the amine compound is an amino alkoxysilane.

2. The process according to claim 1, wherein the ethylenic monomer bearing a $C_8$ to $C_{22}$ linear or branched alkyl group is chosen from:
    a) linear or branched $C_8$-$C_{22}$ alkyl (meth)acrylates;
    b) (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group;
    c) vinyl esters of formula $R_5$—CO—CH=$CH_2$ in which $R_5$ represents a linear or branched $C_8$-$C_{22}$ alkyl group; and
    d) ethers of formula $R_6$—O—CH=$CH_2$ in which $R_6$ represents a linear or branched $C_8$-$C_{22}$ alkyl group.

3. The process according to claim 1, wherein the ethylenic monomer bearing a $C_8$ to $C_{22}$ linear or branched alkyl group is chosen from $C_8$-$C_{22}$.

4. The process according to claim 1, wherein the ethylenic monomer bearing a $C_8$ to $C_{22}$ linear or branched alkyl group is chosen from 2-ethylhexyl acrylate, 2-ethylhexyl methacrylate, lauryl acrylate, lauryl methacrylate, behenyl acrylate, behenyl methacrylate, stearyl acrylate, and stearyl methacrylate.

5. The process according to claim 1, wherein the ethylenic monomer bearing a $C_8$ to $C_{22}$ linear or branched alkyl group is present in said ethylenic polymer in a content ranging from 45% to 90% by weight relative to the total weight of monomers.

6. The process according to claim 1, wherein maleic anhydride is present in said ethylenic polymer in a content ranging from 10% to 25% by weight relative to the total weight of monomers.

7. The process according to claim 1, wherein for said polydimethylsiloxane silicone monomer:
    $R_8$ denotes a methyl group;
    $R_9$ denotes a linear divalent hydrocarbon-based group containing from 2 to 4 carbon atoms;
    $R_{10}$ denotes a linear or branched alkyl group, comprising from 2 to 8 carbon atoms; and
    n denotes an integer ranging from 3 to 200.

8. The process according to claim 1, wherein said additional monomer is non-silicone and is chosen from $C_6$-$C_{12}$ cycloalkyl (meth)acrylates.

9. The process according to claim 1, wherein said ethylenic polymer comprises said additional polydimethylsiloxane silicone monomer.

10. The process according to claim 1, wherein said ethylenic polymer comprises an additional monomer present in a content ranging from 5% to 50% by weight, relative to the total weight of monomers.

11. The process according to claim 1, wherein said ethylenic polymer does not contain any additional monomer.

12. The process according to claim 1, wherein said ethylenic polymer comprises, or consists of:
    (a) 75% to 95% by weight, relative to the total weight of monomers, of linear or branched $C_8$-$C_{22}$ alkyl (meth)acrylate; and
    (b) 5% to 25% by weight of maleic anhydride.

13. The process according to claim 1, wherein said ethylenic polymer is chosen from the following copolymers:
    2-ethylhexyl acrylate/maleic anhydride
    stearyl acrylate/maleic anhydride and
    2-ethylhexyl acrylate/stearyl acrylate/maleic anhydride.

14. The process according to claim 1, wherein said ethylenic polymer comprises, or consists of:
    (a) 45% to 94.5% by weight, relative to the total weight of monomers, of linear or branched $C_8$-$C_{22}$ alkyl (meth)acrylate;
    (b) 5% to 25% by weight of maleic anhydride; and
    (c) 0.5% to 50% by weight of said polydimethylsiloxane silicone monomer.

15. The process according to claim 1, wherein said ethylenic polymer is chosen from the following copolymers:
    2-ethylhexyl acrylate/maleic anhydride/polydimethylsiloxane silicone monomer stearyl acrylate/maleic anhydride/polydimethylsiloxane silicone monomer and 2-ethylhexyl acrylate/stearyl acrylate/maleic anhydride/polydimethylsiloxane silicone monomer.

16. The process according to claim 1, wherein said ethylenic polymer comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride; and
(c) 0.5% to 50% by weight of $C_6$-$C_{12}$ cycloalkyl (meth)acrylate.

17. The process according to claim 1, wherein said ethylenic polymer is chosen from the following copolymers:
2-ethylhexyl acrylate/maleic anhydride/isobornyl (meth)acrylate
stearyl acrylate/maleic anhydride/isobornyl (meth)acrylate and
2-ethylhexyl acrylate/stearyl acrylate/maleic anhydride/isobornyl (meth)acrylate.

18. The process according to claim 1, wherein said ethylenic polymer comprises, or consists of:
(a) 45% to 94.5% by weight, relative to the total weight of monomers, of linear or branched $C_8$-$C_{18}$ alkyl (meth)acrylate;
(b) 5% to 25% by weight of maleic anhydride; and
(c) 0.5% to 50% by weight of a mixture of $C_6$-$C_{12}$ cycloalkyl (meth)acrylate and of silicone monomer (I).

19. The process according to claim 1, wherein said ethylenic polymer is chosen from the following copolymers:
2-ethylhexyl acrylate/maleic anhydride/isobornyl (meth)acrylate/polydimethylsiloxane silicone monomer
stearyl acrylate/maleic anhydride/isobornyl (meth)acrylate/polydimethylsiloxane silicone monomer and
2-ethylhexyl acrylate/stearyl acrylate/maleic anhydride/isobornyl (meth)acrylate/polydimethylsiloxane silicone monomer.

20. The process according to claim 1, wherein the ethylenic polymer has a weight-average molecular weight ranging from 5000 to 1,000,000 g/mol.

21. The process according to claim 1, wherein the ethylenic polymer is present in the composition in a content ranging from 0.1% to 40% by weight, relative to the total weight of the composition.

22. The process according to claim 1, wherein the amine compound is a polyamine compound comprising from 2 to 20 carbon atoms.

23. The process according to claim 1, wherein the amine compound is chosen from N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine.

24. The process according to claim 1, wherein the amine compound is chosen from amine-based polymers.

25. The process according to claim 24, wherein the amine compound is chosen from poly(($C_2$-$C_5$)alkyleneimines); polyvinylamines and copolymers thereof;
vinylamine/vinylformamide copolymers; polyamino acids bearing $NH_2$ groups; amino polyvinyl alcohol, acrylamidopropylamine-based copolymers; chitosans;
polydimethylsiloxanes comprising primary amine groups at the chain end or on side chains;
amodimethicones of formula (D):

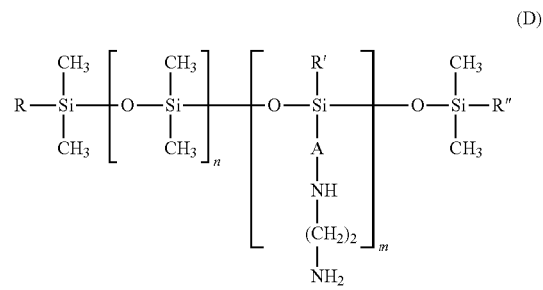

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500,000 approximately;
amodimethicones of formula (K):

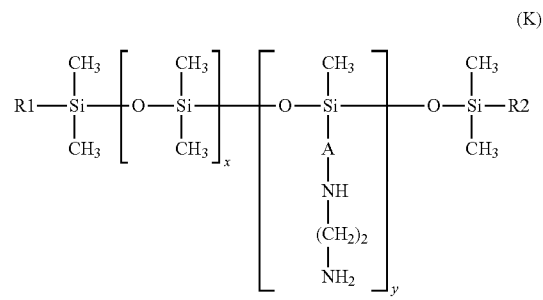

in which:
R1 and R2, which may be identical or different, represent a linear or branched, saturated or unsaturated alkyl group comprising from 6 to 30 carbon atoms,
A represents a linear or branched alkylene radical group containing from 2 to 8 carbon atoms,
x and y are numbers ranging from 1 to 5000;
polytetrahydrofuran (or polytetramethylene glycol) α,ω-diamines and polybutadiene α,ω-diamines;
polyamidoamine dendrimers bearing amine end functions;
poly(meth)acrylates or poly(meth)acrylamides bearing primary or secondary amine side functions; and
polyethylene glycol and/or polypropylene glycol α,ω-diamines; ethylenediamine, 1,3-propylenediamine and 1,4-butylenediamine.

26. The process according to claim 1, wherein the amine compound is an amino alkoxysilane of formula (III):

in which:
$R'_1$ is a linear or branched, saturated or unsaturated, cyclic or acyclic $C_1$-$C_6$ hydrocarbon-based chain substituted with a group chosen from the following groups:
amine $NH_2$ or NHR with R=$C_1$-$C_4$ alkyl, an aryl or aryloxy group substituted with an amino group or with a $C_1$-$C_4$ aminoalkyl group, $R'_1$ optionally being interrupted in its chain with a heteroatom (O, S, NH) or a carbonyl group (CO), $R'_1$ being linked to the silicon atom directly via a carbon atom, $R'_2$ and $R'_3$, which may be identical or different, represent a linear or branched alkyl group comprising from 1 to 6 carbon atoms, z denotes an integer ranging from 1 to 3, and x denotes an integer ranging from 0 to 2, with z+x=3.

27. The process according to claim 1, wherein the amine compound is used in a mole ratio of amine group of the amine compound/maleic anhydride group of the ethylenic polymer ranging from 0.01 to 10.

28. The process according to claim 1, wherein the composition(s) used comprise a hydrocarbon-based oil.

29. The process according to claim 1, wherein the composition comprising the ethylenic polymer contains a silicone oil.

30. The process according to claim 1, wherein the composition comprising the maleic anhydride ethylenic polymer is applied first to the keratin materials, and at least one amine component chosen from an amine compound chosen from amino alkoxysilanes, and a composition containing the amine compound and comprising a physiologically acceptable medium.

31. The process according to claim 1, wherein at least one amine component chosen from an amine compound chosen from amino alkoxysilanes, and a composition containing the amine compound and comprising a physiologically acceptable medium, is applied first to the keratin materials, and the composition comprising the maleic anhydride ethylenic polymer is then applied.

32. The process according to claim 1, wherein a composition derived from mixing of 1) a composition comprising a maleic anhydride acrylic polymer and 2) at least one amine component chosen from an amine compound chosen from amino alkoxysilanes, and a composition containing the amine compound and comprising a physiologically acceptable medium, is applied topically to the keratin materials.

33. The process according to claim 1, wherein the keratin material is selected from the group of skin and lips.

34. A kit comprising a first composition comprising a maleic anhydride ethylenic polymer and a second composition comprising at least one amine component chosen from an amine compound chosen from polyamine compounds bearing several primary amine and/or secondary amine groups and amino alkoxysilanes and optionally comprising a physiologically acceptable medium, the first and second compositions each being packaged in a separate packaging assembly, the compositions being anhydrous when the amine compound is an amino alkoxysilane, said maleic anhydride ethylenic polymer consisting of:

(a) 45% to 95% by weight, relative to the total weight of monomers, of an ethylenic monomer bearing a $C_8$ to $C_{22}$ linear or branched alkyl group chosen from:

i) linear or branched $C_8$-$C_{22}$ alkyl (meth)acrylates;

ii) (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group;

iii) vinyl esters of formula $R_5$—CO—O—CH=$CH_2$ in which $R_5$ represents a linear or branched $C_8$-$C_{22}$ alkyl group; and iv) ethers of formula $R_6$—O—CH=$CH_2$ in which $R_6$ represents a linear or branched $C_8$-$C_{22}$ alkyl group;

(b) 5% to 25% by weight of maleic anhydride; and (c) 0% to 50% by weight of additional monomer chosen from:

(i) polydimethylsiloxane silicone monomers bearing a mono(meth)acryloyloxy end group of formula (I) below:

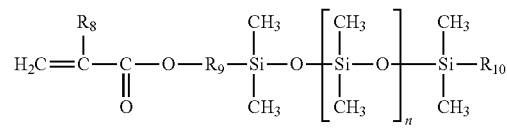

in which:

$R_8$ denotes a hydrogen atom or a methyl group;

$R_9$ denotes a linear or branched divalent hydrocarbon-based group containing from 1 to 10 carbon atoms and optionally containing one or two ether bond —O—;

$R_{10}$ denotes a linear or branched alkyl group containing from 1 to 10 carbon atoms; and n denotes an integer ranging from 1 to 300;

and (ii) linear or branched $C_1$-$C_6$ alkyl (meth)acrylate or $C_6$-$C_{12}$ cycloalkyl (meth)acrylate non-silicone monomers.

35. A composition obtained by mixing an ethylenic polymer, or a composition containing the ethylenic polymer and comprising a physiologically acceptable medium, and at least one amine component chosen from an amine compound chosen from polyamine compounds bearing several primary amine and/or secondary amine groups and amino alkoxysilanes or a composition containing the amine compound and comprising a physiologically acceptable medium, said maleic anhydride ethylenic polymer being a random or gradient polymer consisting of:

(a) 45% to 95% by weight, relative to the total weight of monomers, of an ethylenic monomer bearing a $C_8$ to $C_{22}$ linear or branched alkyl group chosen from:

i) linear or branched $C_8$-$C_{22}$ alkyl (meth)acrylates;

ii) (meth)acrylamides of formula $CH_2$=$C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched C8 to C12 alkyl group;

iii) vinyl esters of formula $R_5$—CO—CH=$CH_2$ in which $R_5$ represents a linear or branched $C_8$-$C_{22}$ alkyl group; and iv) ethers of formula $R_6$—O—CH=$CH_2$ in which $R_6$ represents a linear or branched $C_8$-$C_{22}$ alkyl group;

(b) 5% to 25% by weight of maleic anhydride; and (c) 0 to 50% by weight of additional monomer chosen from:

(i) polydimethylsiloxane silicone monomers bearing a mono(meth)acryloyloxy end group of formula (I) below:

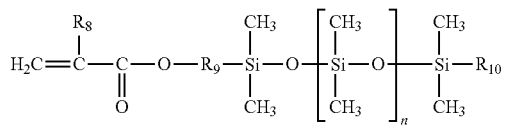

(I)

in which:
- $R_8$ denotes a hydrogen atom or a methyl group;
- $R_9$ denotes a linear or branched divalent hydrocarbon-based group containing from 1 to 10 carbon atoms and optionally containing one or two ether bond —O—;
- $R_{10}$ denotes a linear or branched alkyl group containing from 1 to 10 carbon; and
- n denotes an integer ranging from 1 to 300;

and (ii) linear or branched $C_1$-$C_6$ alkyl (meth)acrylate or $C_6$-$C_{12}$ cycloalkyl (meth)acrylate non-silicone monomers.

36. A polymer that may be obtained by reacting an at least one amine component chosen from an amine compound chosen from polyamine compounds bearing several primary amine and/or secondary amine groups and amino alkoxysilanes with a maleic anhydride ethylenic polymer, the reaction being performed in anhydrous medium when the amine compound is an amino alkoxysilane, said maleic anhydride ethylenic polymer being a random or gradient polymer consisting of:
(a) 45% to 95% by weight, relative to the total weight of monomers, of an ethylenic monomer bearing a $C_8$ to $C_{22}$ linear or branched alkyl group chosen from:
i) linear or branched $C_8$-$C_{22}$ alkyl (meth)acrylates;
ii) (meth)acrylamides of formula $CH_2=C(R_1)$—$CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group;
iii) vinyl esters of formula $R_5$—CO—O—CH=$CH_2$ in which $R_5$ represents a linear or branched $C_8$-$C_{22}$ alkyl group; and
iv) ethers of formula $R_6$—O—CH=$CH_2$ in which $R_6$ represents a linear or branched $C_8$-$C_{22}$ alkyl group;
(b) 5% to 25% by weight of maleic anhydride; and
(c) 0% to 50% by weight of additional monomer chosen from:
(i) polydimethylsiloxane silicone monomers bearing a mono(meth)acryloyloxy end group of formula (I) below:

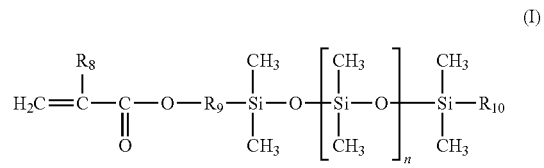

(I)

in which:
- $R_8$ denotes a hydrogen atom or a methyl group;
- $R_9$ denotes a linear or branched divalent hydrocarbon-based group containing from 1 to 10 carbon atoms and optionally containing one or two ether bond —O—;
- $R_{10}$ denotes a linear or branched alkyl group containing from 1 to 10 carbon atoms; and
- n denotes an integer ranging from 1 to 300;

and (ii) linear or branched $C_1$-$C_6$ alkyl (meth)acrylate or $C_6$-$C_{12}$ cycloalkyl (meth)acrylate non-silicone monomers.

37. A composition comprising, in a physiologically acceptable medium, a polymer according to claim 36.

38. The process according to claim 1, wherein the maleic anhydride ethylenic polymer is a random copolymer.

* * * * *